United States Patent
Akiyama et al.

(10) Patent No.: US 11,312,956 B2
(45) Date of Patent: Apr. 26, 2022

(54) NUCLEIC ACID INHIBITING EXPRESSION OF THE MEX3B GENE, MEX3B GENE EXPRESSION INHIBITOR, METHOD FOR INHIBITING MEX3B GENE EXPRESSION, AND PROPHYLACTIC OR THERAPEUTIC AGENT FOR DISEASE CAUSED BY MEX3B GENE EXPRESSION

(71) Applicants: TAK-CIRCULATOR CO., LTD, Tokyo (JP); UNIVERSITY OF TOKYO, Tokyo (JP)

(72) Inventors: Tetsu Akiyama, Tokyo (JP); Yusuke Yamazumi, Tokyo (JP); Kazuyoshi Kofu, Tokyo (JP)

(73) Assignees: TAK-CIRCULATOR CO., LTD, Tokyo (JP); UNIVERSITY OF TOKYO, Tokyo (JP)

( * ) Notice: Subject to any disclaimer, the term of this patent is extended or adjusted under 35 U.S.C. 154(b) by 368 days.

(21) Appl. No.: 16/315,594

(22) PCT Filed: Jul. 7, 2017

(86) PCT No.: PCT/JP2017/025014
§ 371 (c)(1),
(2) Date: Jan. 4, 2019

(87) PCT Pub. No.: WO2018/008749
PCT Pub. Date: Jan. 11, 2018

(65) Prior Publication Data
US 2021/0079390 A1 Mar. 18, 2021

(30) Foreign Application Priority Data
Jul. 8, 2016 (JP) .............................. JP2016-136401

(51) Int. Cl.
*A61K 48/00* (2006.01)
*C12N 15/113* (2010.01)

(52) U.S. Cl.
CPC .................................. *C12N 15/113* (2013.01)

(58) Field of Classification Search
CPC ..................................................... C07H 21/04
See application file for complete search history.

(56) References Cited

U.S. PATENT DOCUMENTS

| 8,962,244 | B2 | 2/2015 | Ryder |
| 2003/0049662 | A1 | 3/2003 | Monia et al. |
| 2003/0152956 | A1 | 8/2003 | Ohtani et al. |
| 2005/0261219 | A1 | 11/2005 | Richards et al. |
| 2008/0172930 | A1 | 8/2008 | Akiyame et al. |
| 2009/0118213 | A1 | 5/2009 | Hansen et al. |
| 2011/0200612 | A1 | 8/2011 | Schuster et al. |
| 2011/0256063 | A1 | 10/2011 | Lu et al. |
| 2012/0183538 | A1 | 7/2012 | Trieu et al. |
| 2012/0244170 | A1 | 9/2012 | Ciosk et al. |
| 2014/0350083 | A1 | 11/2014 | Fire et al. |

FOREIGN PATENT DOCUMENTS

| JP | 2002508944 A | 3/2002 |
| JP | 2003520586 A | 7/2003 |
| JP | 4155561 B2 | 9/2008 |
| JP | 2009507499 A | 2/2009 |
| JP | 442 9269 | 12/2009 |
| JP | 2011 526892 | 10/2011 |
| JP | 2012532613 A | 12/2012 |
| WO | 99 32619 | 7/1999 |
| WO | WO09949065 A1 | 9/1999 |
| WO | 2002031136 A1 | 4/2002 |
| WO | 03 040182 | 5/2003 |
| WO | 2015/155710 A1 | 4/2015 |

OTHER PUBLICATIONS

Buchet-Poyau, et al., "Identification and Characterization of Human Mex-3 Proteins, a Novel Family of Evolutionarily Conserved RNA-Binding Proteins Differentially Localized to Processing Bodies," Nucleic Acids Research, 2007, vol. 35, No. 4, 1289-1300.
Mandiyan, et al., "Molecular and Cellular Characterization of Baboon C-Raf as a Target for Antiproliferative Effects of Antisense Oligonucleotides," Antisense and Nucleic Acid Drug Development, 1997, vol. 7, 539-548.
Wolozin, et al., "Participation of Presenilin 2 Apoptosis: Enhanced Basal Activity Conferred by an Alzheimer Mutation," Science, Dec. 6, 1996, vol. 274, 1710-1713.
Yoon, et al., "Scaffold Function of Long Non-Coding RNA HOTAIR in Protein Ubiquitination," Nature Communications, Dec. 11, 2013, www.nature.com/nturecommunications.
Yamazumi et al., "RNA Binding Protein Max-3B is Required for IL-33 Induction in the Development of Allergic Airway Inflammation," Cell Rep., Aug. 2016, vol. 16, 2456-2471.
WIPO, WO 2018/008749, Jan. 11, 2018, "International Search Report of PCT/JP2017/025014".

(Continued)

*Primary Examiner* — Kimberly Chong
(74) *Attorney, Agent, or Firm* — Emerson Thomson Bennett; Daniel A. Thomson

(57) ABSTRACT

A nucleic acid which can inhibit expression of the MEX3B gene with low cytotoxicity as a side effect, an MEX3B gene expression inhibitor which contains said nucleic acid, a method for inhibiting MEX3B gene expression, and a prophylactic or therapeutic agent for disease caused by MEX3B gene expression are provided.
This nucleic acid, which inhibits the expression of the MEX3B gene, is an antisense oligonucleotide having a sequence complementary to an oligonucleotide that contains at least 10 contiguous nucleotides in an untranslated region in an exon of the MEX3B gene, or
   a double-stranded RNA including at least 20 contiguous nucleotides in the aforementioned untranslated region, or DNA encoding said double-stranded RNA.

1 Claim, 3 Drawing Sheets
Specification includes a Sequence Listing.

(56) References Cited

OTHER PUBLICATIONS

Draper, et al., "MEX-3 is a KH Domain Protein that Regulates Blastomere Identity in Early C. Elegans Embryos," Cell, vol. 87, 205-216, Oct. 1996.
EP Office, "Supplemental Search Report," dated May 6, 2019.
EP Office, "Office Action," dated May 21, 2019.
Hagedorn, et al., "Managing the Sequence-Specificity of Antisense Oligonucleotides in Drug Discovery," Nucleic Acids Research, 2017, vol. 45, No. 5, pp. 2262-2282.
Fakhr, et al., "Precise and Efficient siRNA Design: A Key Point in Competent Gene Silencing," Cancer Gene Therappy, 2016, vol. 23, pp. 73-82.
Office Action dated Jan. 8, 2021 for U.S. Appl. No. 16/315,513.
Abstract of EP1347051A1 corresponding to JP4155561B2.
Qui, et al., "Bronchial Mucosal Inflammation and Upregulation of CXC Chemoattractants and Receptors in Severe Exacerbations of Asthma," Thorax, 2007, vol. 62, pp. 475-482.
Chung, et al., "Cytokines in Asthma," Thorax, 1999, vol. 54, pp. 825-857.
Corren, et al., "Lebrikizumab Treatment in Adults with Asthma," The New England Journal of Medicine, N Engl J Med 365;12, Sep. 22, 2011, pp. 1088-1098.
Shifren, et al., "Mechanisms of Remodeling in Asthmatic Airways," Hindawi Publishing Corporation, Journal of Allergy, Division of Pulmonary and Critical Care Medicine, Washington University School of Medicine, St. Louis, MO 63110, USA, Oct. 10, 2011, vol. 2012, Article ID 316049, pp. 1-12.
Zhu, et al., "Mex3B: a Coreceptor to Present dsRNA to TLR3," Cell Research (2016), vol. 26, pp. 391-392.
Sadik, et al., "Neutrophils Cascading their way to Inflammation," NIH Public Access Author Manuscript, Trends Immunol, Oct. 2011, vol. 32(10), pp. 452-460.
Robinson, et al., "Predominant Th2-Like Bronchoalveolar T-Lymphocyte Population in Atopic Asthma," The New England Journal of Medicine, Jan. 30, 1992, vol. 326, No. 5, pp. 298-304.
LeBorgne, et al., "The RNA-Binding Protein Mex3b Regulates the Spatial Organization of the Rap1 Pathway," The Company of Biologists, Ltd., 2014,. vol. 141, pp. 2096-2107.

Brightling, et al., "Targeting TNF-α: A Novel Therapeutic Approach for Asthma," Europe PMC Funders Group, Author Manuscript, J. Allergy Clin Immunol, Jan. 2008, vol. 121(1), 5-12, pp. 1-15.
Morishima, et al., Th17-Associated Cytokines as a Therapeutic Target for Steroid-Insensitive Asthma, Hindawi Publishing Corporation, Clinical and Developmental Immunology, vol. 2013, Article ID 609395, pp. 1-9.
Al-Ramli, et al., "TH-17 Cell-Related Cytokines' Potential Role in the Pathogenesis of Severe Asthma," Journal of Asthma, vol. 45(S1), 2008, pp. 41-44.
Bradley, "TNF-mediated Inflammatory Disease," NIHR Cambridge Biomedical Research Centre, Addenbrooke's Hospital, Cambridge, UK, Pathological Society of Great Britain and Ireland, Journal of Pathology, J Pathol 2008; vol. 214: pp. 149-160.
International Search Report dated Aug. 3, 2017 for International Application No. PCT/JP2017/025015.
Translation of International Search Report dated Aug. 3, 2017 for International Application No. PCT/JP2017/025015.
Office Action dated Mar. 13, 2018 for Japanese Patent Application No. JP2017-559904.
Yang, et al., "The RNA-Binding Protein Mex3B is a Coreceptor of Toll-like Receptor 3 in Innate Antiviral Response," Wuhan Institute of Virology, State LKey Laboratory of Virology, Chinese Academy of Sciences, Hubei 430071, China Collaborative Innovation Center for Viral Immunology, Medical Research Institute College of Life Sciences, Wuhan University, Hubei 430072, China, Cell Research, 2016, vol. 26, pp. 288-303.
Kang, et al., "Therapeutic uses of Anti-Interleukin-6 Receptor Antibody," International Immunology, The Japanese Society for Immunology, 2014, vol. 27, No. 1, pp. 21-29.
Supplementary European Search Report dated Jun. 14, 2019 for Application Serial No. EP 17824353.
Office Action dated Jul. 16, 2019 for Application Serial No. EP 17824353.
Kurreck, J et al. ; "Design of antisense oligonucleotides stabilized by locked nucleic acids"; Nucleic Acids Research; 2002; vol. 30(9); p. 1911-1918.
Seth, P. et al.; "Structure Activity Relationships of a-L-LNA Modified Phosphorothioate Gapmer Antisense Oligonucleotides in Animals"; Molecular Therapy-Nuclecic Acids; 2012; vol. 1, e47; p. 1-8.

SEQUENCE LISTING

<160> NUMBER OF SEQ ID NOS: 26

<210> SEQ ID NO 1
<211> LENGTH: 3532
<212> TYPE: DNA
<213> ORGANISM: Human

```
<400> SEQUENCE: 1
tcaagaggcg gggaggagag gaggaaaaag cgctgagtga gggcgggcgg gcgggcggga      60
gggagggagt ggaggagccg gggaggggct ccttaaagaa acgcttctgt cgctcgcctg     120
ctcgcttttc gctcggcatt gcggccagcc agccgggcac tcgggggggca cgcgcggcca    180 ccgctagagc tctgccccca ccccacccgc cagcaggtct ggggtgggga cccaggtggg     240
ggctcctgca gccactgccc ggtgcggacc gcacggagcg acccactcct cccagcaccg     300
aggaagaagc aacggagccc tcagcaggcg accggcctcc ccgcccctga ccacccgctt    360
cccggctgcc tttgtggccg cagcttctcg ccgccgagcc gagggccggc ggggcgcgg     420 cgcgcacggc cgagcgatgc ccagctcgct gttcgcagac ctggagcgca acggcagcgg    480
cggcggcggc ggcggcagca gcggaggggg agagaccctg gatgaccaaa gagccctgca    540
gctcgcgctc gaccagctct ccctgctggg gctggacagt gacgagggcg cctctctgta    600
cgacagcgag ccgcgcaaga gagcgtgaaa catgaccgag tgcgtgccag tacccagttc    660
tgagcatgtc gccgagatcg tggggcggca aggttgtaaa atcaaagcgc tgcgggcgaa    720
gaccaatact tacatcaaga ccccagttcg cggggaggag cctgtctttg ttgtgacggg    780
caggaaggag gatgtgggca tggctcggag ggagatcatc tctgctgccg agcacttctc    840
catgatccgc gcctcccgga ataagaacac ggcactcaac ggcgcggtgc ctgggccgcc    900
caacctgccc gggcagacca ccatccaagt gcgggtaccc taccgcgtgg tggggctcgt    960
ggtgggcccc aaaggcgcca caatcaagcg catccagcag cagacgcaca cgtacatcgt   1020
gacgcccagc cgggataagg agccggtgtt cgaggtgacc ggcatgccag agaacgtgga   1080
tcgcgctcga gaggagattg aggcgcacat tgctctgcgt accggcggca tcattgagct   1140
cacagacgag aacgacttcc acgccaacgg caccgatgtg ggcttcgatc tgcatcatgg   1200
gtccggcggg tccggcccag gcagcctctg gagcaagccc accccagca tcacgcccac   1260 cccccggccgc aagcctttct ctagctaccg caacgcacag tccagctcgc ttggcagtgc   1320
ttccacagac tcttatttcg gcggcgggac cagcagcagc gcagcggcta cccagcgcct   1380
ggcggactac agccccccta gccccgccct gagctttgcg cacaacggaa acaataacaa   1440
taacggcaat gggtacacct acacagcggg gggagaagcc tcagtgccat cccccgacgg   1500
ctgccccgag ctgcagccca cttttgaccc ggctcccgct cccccacctg ggcaccact    1560 tatctgggcc cagttcgagc ggtccccggg aggcggacct gcagctccgg tatcttcttc   1620
ctgctcttct tctgcatctt cgtctgcttc ttcctcctcc gtggtcttcc ccggggtgg    1680 cgccagtgcg ccctccaacg ccaacctggg gctattggtg caccgccggc tgcaccctgg   1740
caccagctgc ccgcgcctgt ctccacccctt gcacatggcc ccggggcgg gagagcacca   1800 cctggctcgc cgggtgcgca cgacccgggg tggaggaggc ctggcctacg ccgcttatgc   1860
caacgggctg ggggcacagc tgcctggctt gcagccgtcg gacacgtcgg gctcctcctc   1920
ttcgtccagc tcctcctcca gctcttcatc ctcttcctcc gggcttcggc gtaaaggcag   1980
ccgcgactgc tccgtgtgct tcgagagcga agtgattgcc gcgctggtgc cctgtggcca   2040
caacctcttc tgcatggagt gcgccaatcg catctgtgag aagagcgagc ccgagtgccc   2100
ggtctgccac accgcggtca ctcaggccat ccgcatcttt tcttaaaggc agcgggcgct   2160
gctagtgcgc accgtgctgg ggaaggggg aaccccctccc catcctcttt ccccagcgct   2220
cgcctgcctc cctgggtgcc ccccctctcc cttctccttc ccggcccac caacactctg    2280 agatccgaga ggagcttgga aagctgtagt atccgctcat ttttaaaatt taattttaa    2340
```

| | | | | |
|---|---|---|---|---|
| gtaaaggaat | tgccaggat | atctgcatca | agagtactgt | agcctgggaa acctgaacac | 2400 |
| ctgaaatgca | tgctctataa | ataataggaa | cggcgacatt | ctagtaatga tagttttttac | 2460 |
| actgtactta | ataggaagct | tccaaaagaa | gaaaacccca | caagttttcc attttcttaa | 2520 |
| agtaggaaaa | aatgaacagt | aataattatg | atgaagatga | tagtagtgct atgggatgtg | 2580 |
| tggactgttt | agtgtgttcc | cctttgtggg | tgggttccta | tgatacttat tatagaacac | 2640 |
| agtggatcct | ttttgaatgt | tcgtggaagg | gccaggagtt | cctgtgaaac caggatactg | 2700 |
| cagctttatt | aaagttaaag | aaactgtaac | atatctctta | tatattaaaa acgtttaaaa | 2760 |
| gttttaaaga | gaaattgcat | taatacagat | tgaagtattt | tattcttttt tgacttgaaa | 2820 |
| aattatattt | catattgcaa | agatgtttac | aagtattta | atttaagttc agtgaacttt | 2880 |
| tttgtagctg | ggttaaatct | ttttatttta | gtatggcctt | atggcaaaga acactgtatt | 2940 |
| attttaataa | tcacacaatt | gtgacggaat | tacaaccata | aaatgtgtaa tgttttgaac | 3000 |
| agtattctgt | tgggatggag | attttatagg | ttcagacaaa | tcttctagat ctgcttcacc | 3060 |
| cagcatattt | tctattcagt | gatataaagc | atattttatt | ctatattatt acaaaaacgg | 3120 |
| aaatgtataa | acatgtcaaa | aagaactgtt | gatgctttct | aacatttgta taaatagaat | 3180 |
| tcagtgcaag | ttacaaaaat | tctgttgcac | cactctagtt | ttagtatttc tattttaata | 3240 |
| catttgttta | ccacttgttt | atgtatatgt | aggtgatgtt | acttgagctt aaatgtactt | 3300 |
| tactgagcaa | agtttaaaaa | acaaagtata | ttttatttta | tgataaaggg cctttaacct | 3360 |
| catggtcaaa | tactaatatt | atatttgctg | agacaagatt | tgaaattgta tcaagagttt | 3420 |
| tatttttctg | acatttaaag | ttctacataa | taaaggtaaa | acttaagtaa tggtgctact | 3480 |
| tcatttttta | agtatttcta | tataaataaa | atattgaaga | aaatcttaaa aa | 3532 |

<210> SEQ ID NO 2
<211> LENGTH: 3416
<212> TYPE: DNA
<213> ORGANISM: Mouse

<400> SEQUENCE: 2

| | | | | |
|---|---|---|---|---|
| tgttcgcttt | gcgctcggca | ttgtggccag | ccagccgggc | actcgggggg cacgcgcggc | 60 |
| cgccgctcga | gctctgcccc | caccccaacc | gccagcagat | ctggggtggg gacccaggcg | 120 |
| ggggctcttg | cagccactgc | ccggtgcgga | ttgcacgcag | agaccactc ctccgagcgc | 180 |
| cgaaaaacga | gccacggagc | cctccgcagc | cgaccggcct | ccccgcccct gactgccggc | 240 |
| ttcccggctg | ccttttgtggc | tgcaccttct | agctgccgag | cagagagccg gctggggcgc | 300 |
| ggcgcgcacg | gcggagcgat | gcccagctcg | ctgtttgcag | acctggagcg caacggcagc | 360 |
| ggcggcggcg | ggggaggcgg | cggcggggga | ggcggcggtg | gcagcggcgg gggagagact | 420 |
| ctggatgacc | aaagagccct | gcagcttgcg | ctcgatcagc | tctccctgtt gggactggac | 480 |
| agtgatgagg | gcgcctcttt | gtacgacagc | gaaccgcgca | agaagagcgt gaacatgacc | 540 |
| gagtgcgtgc | cggtacccag | ttccgaacac | gtcgcggaga | tcgtagggag gcaaggttgt | 600 |
| aaaatcaaag | ctttgaggc | gaagaccaac | acttacatca | agaccccagt tcgcggggag | 660 |
| gagcctgtct | ttgttgtgac | gggcaggaag | gaggatgtgg | ctatggctcg gagggagatc | 720 |
| atctctgccg | cagagcactt | ctccatgatc | cgagcctctc | gtaacaagaa cacggctctc | 780 |
| aacggagctg | tgcccggacc | gcccaacctg | ccgggacaga | ccactatcca agtgagggtg | 840 |
| ccataccgcg | tggtagggct | cgtggtgggt | ccaaagggcg | ccacgatcaa gcgcattcaa | 900 |

```
cagcagacac atacatatat tgtgacaccc agccgagaca aggagccagt tttcgaggtg    960
actggcatgc cagagaacgt ggatcgcgct agagaggaga tcgaagctca catcgcgctg   1020
cgcaccggtg gcatcatcga gctgacagac gagaacgact ccatgccaa tggcacagac    1080
gtgggctttg atctgcatca cgggtccggc gggtccgggc cggcagcct ctggagcaag    1140
cccacccccaa gcatcactcc tacacctggc cgcaagccct tctccagcta tcgcaacgac   1200
agctccagct cgcttggcag cgcatccaca gactcttact tcggtggtgg gaccagcggc   1260
agcgcagctg ctacttcacg cctggcggac tatagccctc ccagccctgc actcagcttt    1320
gctcacaatg ggaacaacaa caataacggc aatggttaca cctacacagc gggggaagcc   1380
tcagtacctt ccccagatgg gggtcctgag ctgcagccta ctttcgaccc agctcccgcc   1440
ccaccacctg gcacacccct tctctgggcc cagttcgagc gctctccagg aggtggatct   1500
gcagcaccag tatcctcttc ctgctcttct tcggcatcct catctgcctc gtcgtcctct   1560
gtggtctttc ccggggtgg cgccagcagc acaccctcca atgccaatct ggggctgctg    1620
gtgcaccgtc gactgcaccc gggcaccagc tgccgcgcc tgtctccgcc cttgcacatg    1680
gccacggggg cgggagagca ccaccttgct cgccgcgtgc gcagcgaccc gggcggtgga   1740
ggcctggcct acgctgccta tgctaatggg ctagggacga agctccctgg cctgccctcg   1800
tcggacactt cgggctcctc ctcgtcctct agctcctcct ccagctcttc ctcctcttcc    1860
tctgggctga ggcgcaaagg cagccgcgac tgctctgtgt gcttcgagag tgaagtgatc    1920
gccgcgctgg tgccctgtgg ccacaacctc ttctgcatgg agtgtgccaa ccgcatttgt   1980
gagaagagcg agcccgagtg tcccgtctgc cacacggcgg tcactcaggc catccgcatt    2040
tttcctgaa ggcagtgcgc gcgcgcgcac tgcagggaag agggtcctc tctcgaccct     2100
cattccctag ggtctacctg cccagacgcc tctggtgccc acctctttcc accccaccct   2160
catcactctc agagatccca gaggagcttg gaaagctgta gtatccgctc atttttaaaa   2220
tgtcatttt aaacaaagga acttgccagg atctctgcat caggagtact gtagcctccg    2280
aaccacctga attgcatgct ctataaataa taggaacggc gacattctag taacgatagt   2340
ttttacactg tacttaatag gaagcttcca aaagaaaacc ccacaagttt tccatttttct   2400
tgaagtagaa aaatgaacag taattatgaa gatgattaat aattgtgcta tgggatgtgt    2460
ggactgtttt gtgtgtttcc cttttgtgggt gggttcctac agcgctcgtt ctagaacaca   2520
agtggatcct ttttgaatgt tcatggaagg gccaggagtt ctgtacagcc aggaccctgc   2580
agctttatta aagttaaaac tgtaacatat ctcttatata ttaaaaaaaa aaacctttaa   2640
aagttttaaa gagaaattgc attaatacag attgaagtat tttattcttt ttttgacttg    2700
aaaaattata tttcatattg caaagatgtt tacaagtatt ttaatttaag ttcagtgaac   2760
ttttttgtag ctgggttaaa tcttttttatt tttagtatgg ccttatggca aagaacactg   2820
tattatttta ataatcacac gattgtgacg gattacaaac cataaaatgt ataacgttttt   2880
gagcagtatt ctgttgggat ggagattttta taggttcaga caaatcttct agatctgctt   2940
cacccagcat attttctatt cagtgatata aagcatattt tattctatat tattacaaaa   3000
aatgaaatgt tataaacatg tcaaaaggaa cagttgatgc tttctaacat ttgtatataaat  3060
agaattcagt gcaaattaca gaaattctgt tgcaccgcta tagttttagt gtttctatttt   3120
taatacattt gtttaccact cgtttatgta tatgtaggtg acgttacttg agcttaaatg   3180
tactttactg agcaaagttt aaaaaaaaac aaagtatatt ttatttttatg ataaagggcc   3240
tttaacctca tggtcaaata ctaatattat atttgctgag acaagatttg aaattgtatc    3300
```

```
aagagtttta tttttctgac atttaaagtt ctacataata aaggtaaact taagtaatgg    3360
tgctacttca tttttttaagt atttctatat aaataaaaca ttgaagaaaa atcact       3416
```

<210> SEQ ID NO 3
<211> LENGTH: 836
<212> TYPE: DNA
<213> ORGANISM: Human

<400> SEQUENCE: 3

```
gtaggtcgag gagggatggg gaggtgggtg ggggtggtgt agggtctcag gccactgcct      60 cgagggggaag gcgtgttcag tatcgggatc cgcggcgtgg ggtgccttgg ggagagagga    120
agagccgcgc gatgggccgg cgccccagac aaagaaagtg caggcaggct gtctcccgga    180
gccgcgccgc tgccctggcg ggatgcactt tcttctgcta aaatcactgc cttctcccct    240 aacgccccc aaccagccca cctccagaaa gacaatttaa atgtaagatg cttgggggag     300
ggggcctttg atcagtcctt tggaggagg aaggaggagg agtgagcata ggatgggagg     360
aggattctgg atttctgcaa agcggaatgg agcccagagg aggaacaatg ggtcccggga    420
ctcacacccc acccctacc cccagtcgac cagcgctgag gcatcgcgac ttcagctgcc     480
ttccccgagc cccttccccg tgtcttcaga gctgacggcg cgcccagctg gatcccagcg    540
gcatctcccc agatgacttt tctgggattc tcgggtttgg ttcgggacga ctgcagtcac    600
tgggggaggg ccaggcagcc aatgggctgt tcctcgagcg cctcgcgggt gggatccgct    660
gcccagcccg tggcgcggcc cgaggtcagt gagggagacg cccccttttcc gcccatctct    720 tgtcctgccg tctcgctgtc ctggacgcgg gctgtccccg gtcccgcgg ttaccccagg     780 ataatgggcg tgtctgtctc tctctcccac tccctcctcc gcaccctggt tcgtag         836
```

<210> SEQ ID NO 4
<211> LENGTH: 569
<212> TYPE: PRT
<213> ORGANISM: Human

<400> SEQUENCE: 4

```
Met Pro Ser Ser Leu Phe Ala Asp Leu Glu Arg Asn Gly Ser Gly Gly
1               5                   10                  15

Gly Gly Gly Gly Ser Ser Gly Gly Gly Glu Thr Leu Asp Asp Gln Arg
            20                  25                  30

Ala Leu Gln Leu Ala Leu Asp Gln Leu Ser Leu Leu Gly Leu Asp Ser
        35                  40                  45

Asp Glu Gly Ala Ser Leu Tyr Asp Ser Glu Pro Arg Lys Lys Ser Val
    50                  55                  60

Asn Met Thr Glu Cys Val Pro Val Pro Ser Ser Glu His Val Ala Glu
65                  70                  75                  80

Ile Val Gly Arg Gln Gly Cys Lys Ile Lys Ala Leu Arg Ala Lys Thr
                85                  90                  95

Asn Thr Tyr Ile Lys Thr Pro Val Arg Gly Glu Glu Pro Val Phe Val
            100                 105                 110

Val Thr Gly Arg Lys Glu Asp Val Ala Met Ala Arg Arg Glu Ile Ile
        115                 120                 125

Ser Ala Ala Glu His Phe Ser Met Ile Arg Ala Ser Arg Asn Lys Asn
    130                 135                 140

Thr Ala Leu Asn Gly Ala Val Pro Gly Pro Pro Asn Leu Pro Gly Gln
145                 150                 155                 160
```

```
Thr Thr Ile Gln Val Arg Val Pro Tyr Arg Val Gly Leu Val Val
            165                 170                 175
Gly Pro Lys Gly Ala Thr Ile Lys Arg Ile Gln Gln Thr His Thr
        180                 185                 190
Tyr Ile Val Thr Pro Ser Arg Asp Lys Glu Pro Val Phe Glu Val Thr
        195                 200                 205
Gly Met Pro Glu Asn Val Asp Arg Ala Arg Glu Glu Ile Glu Ala His
    210                 215                 220
Ile Ala Leu Arg Thr Gly Gly Ile Ile Glu Leu Thr Asp Glu Asn Asp
225                 230                 235                 240
Phe His Ala Asn Gly Thr Asp Val Gly Phe Asp Leu His His Gly Ser
                245                 250                 255
Gly Gly Ser Gly Pro Gly Ser Leu Trp Ser Lys Pro Thr Pro Ser Ile
                260                 265                 270
Thr Pro Thr Pro Gly Arg Lys Pro Phe Ser Ser Tyr Arg Asn Asp Ser
            275                 280                 285
Ser Ser Ser Leu Gly Ser Ala Ser Thr Asp Ser Tyr Phe Gly Gly Gly
        290                 295                 300
Thr Ser Ser Ala Ala Ala Thr Gln Arg Leu Ala Asp Tyr Ser Pro
305                 310                 315                 320
Pro Ser Pro Ala Leu Ser Phe Ala His Asn Gly Asn Asn Asn Asn
                325                 330                 335
Gly Asn Gly Tyr Thr Tyr Thr Ala Gly Gly Glu Ala Ser Val Pro Ser
                340                 345                 350
Pro Asp Gly Cys Pro Glu Leu Gln Pro Thr Phe Asp Pro Ala Pro Ala
            355                 360                 365
Pro Pro Pro Gly Ala Pro Leu Ile Trp Ala Gln Phe Glu Arg Ser Pro
370                 375                 380
Gly Gly Gly Pro Ala Ala Pro Val Ser Ser Ser Cys Ser Ser Ser Ala
385                 390                 395                 400
Ser Ser Ser Ala Ser Ser Ser Val Val Phe Pro Gly Gly Gly Ala
                405                 410                 415
Ser Ala Pro Ser Asn Ala Asn Leu Gly Leu Leu Val His Arg Arg Leu
            420                 425                 430
His Pro Gly Thr Ser Cys Pro Arg Leu Ser Pro Pro Leu His Met Ala
        435                 440                 445
Pro Gly Ala Gly Glu His His Leu Ala Arg Arg Val Arg Ser Asp Pro
        450                 455                 460
Gly Gly Gly Gly Leu Ala Tyr Ala Ala Tyr Ala Asn Gly Leu Gly Ala
465                 470                 475                 480
Gln Leu Pro Gly Leu Gln Pro Ser Asp Thr Ser Gly Ser Ser Ser Ser
                485                 490                 495
Ser Ser Ser Ser Ser Ser Ser Ser Ser Ser Ser Gly Leu Arg Arg
                500                 505                 510
Lys Gly Ser Arg Asp Cys Ser Val Cys Phe Glu Ser Glu Val Ile Ala
            515                 520                 525
Ala Leu Val Pro Cys Gly His Asn Leu Phe Cys Met Glu Cys Ala Asn
        530                 535                 540
Arg Ile Cys Glu Lys Ser Glu Pro Glu Cys Pro Val Cys His Thr Ala
545                 550                 555                 560
Val Thr Gln Ala Ile Arg Ile Phe Ser
                565
```

-continued

```
<210> SEQ ID NO 5
<211> LENGTH: 576
<212> TYPE: PRT
<213> ORGANISM: Mouse

<400> SEQUENCE: 5
```

| | | | | | | | | | | | | | | |
|---|---|---|---|---|---|---|---|---|---|---|---|---|---|---|
| Met | Pro | Ser | Ser | Leu | Phe | Ala | Asp | Leu | Glu | Arg | Asn | Gly | Ser | Gly |
| 1 | | | | 5 | | | | | 10 | | | | | 15 |
| Gly | Gly | Gly | Gly | Gly | Gly | Gly | Gly | Gly | Gly | Ser | Gly | Gly | Gly | |
| | | | 20 | | | | | 25 | | | | | 30 | |
| Glu | Thr | Leu | Asp | Asp | Gln | Arg | Ala | Leu | Gln | Leu | Ala | Leu | Asp | Gln | Leu |
| | | | 35 | | | | 40 | | | | | 45 | | | |
| Ser | Leu | Leu | Gly | Leu | Asp | Ser | Asp | Glu | Gly | Ala | Ser | Leu | Tyr | Asp | Ser |
| 50 | | | | | 55 | | | | | 60 | | | | | |
| Glu | Pro | Arg | Lys | Lys | Ser | Val | Asn | Met | Thr | Glu | Cys | Val | Pro | Val | Pro |
| 65 | | | | | 70 | | | | 75 | | | | | | 80 |
| Ser | Ser | Glu | His | Val | Ala | Glu | Ile | Val | Gly | Arg | Gln | Gly | Cys | Lys | Ile |
| | | | | 85 | | | | | 90 | | | | | 95 | |
| Lys | Ala | Leu | Arg | Ala | Lys | Thr | Asn | Thr | Tyr | Ile | Lys | Thr | Pro | Val | Arg |
| | | | 100 | | | | | 105 | | | | | 110 | | |
| Gly | Glu | Glu | Pro | Val | Phe | Val | Val | Thr | Gly | Arg | Lys | Glu | Asp | Val | Ala |
| | | | | 115 | | | | | 120 | | | | | 125 | |
| Met | Ala | Arg | Arg | Glu | Ile | Ile | Ser | Ala | Ala | Glu | His | Phe | Ser | Met | Ile |
| | 130 | | | | | 135 | | | | | 140 | | | | |
| Arg | Ala | Ser | Arg | Asn | Lys | Asn | Thr | Ala | Leu | Asn | Gly | Ala | Val | Pro | Gly |
| 145 | | | | | 150 | | | | | 155 | | | | | 160 |
| Pro | Pro | Asn | Leu | Pro | Gly | Gln | Thr | Thr | Ile | Gln | Val | Arg | Val | Pro | Tyr |
| | | | | 165 | | | | | 170 | | | | | 175 | |
| Arg | Val | Val | Gly | Leu | Val | Val | Gly | Pro | Lys | Gly | Ala | Thr | Ile | Lys | Arg |
| | | | 180 | | | | | 185 | | | | | 190 | | |
| Ile | Gln | Gln | Gln | Thr | His | Thr | Tyr | Ile | Val | Thr | Pro | Ser | Arg | Asp | Lys |
| | | | | 195 | | | | | 200 | | | | | 205 | |
| Glu | Pro | Val | Phe | Glu | Val | Thr | Gly | Met | Pro | Glu | Asn | Val | Asp | Arg | Ala |
| | 210 | | | | | 215 | | | | | 220 | | | | |
| Arg | Glu | Glu | Ile | Glu | Ala | His | Ile | Ala | Leu | Arg | Thr | Gly | Gly | Ile | Ile |
| 225 | | | | | 230 | | | | | 235 | | | | | 240 |
| Glu | Leu | Thr | Asp | Glu | Asn | Asp | Phe | His | Ala | Asn | Gly | Thr | Asp | Val | Gly |
| | | | | 245 | | | | | 250 | | | | | 255 | |
| Phe | Asp | Leu | His | His | Gly | Ser | Gly | Gly | Ser | Gly | Pro | Gly | Ser | Leu | Trp |
| | | | 260 | | | | | 265 | | | | | 270 | | |
| Ser | Lys | Pro | Thr | Pro | Ser | Ile | Thr | Pro | Thr | Pro | Gly | Arg | Lys | Pro | Phe |
| | | | | 275 | | | | | 280 | | | | | 285 | |
| Ser | Ser | Tyr | Arg | Asn | Asp | Ser | Ser | Ser | Leu | Gly | Ser | Ala | Ser | Thr | |
| | 290 | | | | | 295 | | | | | 300 | | | | |
| Asp | Ser | Tyr | Phe | Gly | Gly | Gly | Thr | Ser | Gly | Ser | Ala | Ala | Thr | Ser | |
| 305 | | | | | 310 | | | | | 315 | | | | | 320 |
| Arg | Leu | Ala | Asp | Tyr | Ser | Pro | Ser | Pro | Ala | Leu | Ser | Phe | Ala | His | |
| | | | | 325 | | | | | 330 | | | | | 335 | |
| Asn | Gly | Asn | Asn | Asn | Asn | Gly | Asn | Gly | Tyr | Thr | Tyr | Thr | Ala | Gly | |
| | | | 340 | | | | | 345 | | | | | 350 | | |
| Glu | Ala | Ser | Val | Pro | Ser | Pro | Asp | Gly | Gly | Pro | Glu | Leu | Gln | Pro | Thr |
| | | | 355 | | | | | 360 | | | | | 365 | | |
| Phe | Asp | Pro | Ala | Pro | Ala | Pro | Pro | Gly | Thr | Pro | Leu | Leu | Trp | Ala | |
| | 370 | | | | | 375 | | | | | 380 | | | | |

```
Gln Phe Glu Arg Ser Pro Gly Gly Gly Ser Ala Pro Val Ser Ser
385                 390                 395                 400

Ser Cys Ser Ser Ser Ala Ser Ser Ala Ser Ser Ser Val Val
            405                 410                 415

Phe Pro Gly Gly Gly Ala Ser Thr Pro Ser Asn Ala Asn Leu Gly
            420                 425                 430

Leu Leu Val His Arg Arg Leu His Pro Gly Thr Ser Cys Pro Arg Leu
            435                 440                 445

Ser Pro Pro Leu His Met Ala Thr Gly Ala Gly Glu His His Leu Ala
            450                 455                 460

Arg Arg Val Arg Ser Asp Pro Gly Gly Gly Leu Ala Tyr Ala Ala
465                 470                 475                 480

Tyr Ala Asn Gly Leu Gly Thr Gln Leu Pro Gly Leu Pro Ser Ser Asp
            485                 490                 495

Thr Ser Gly Ser Ser Ser Ser Ser Ser Ser Ser Ser Ser
            500                 505                 510

Ser Ser Ser Gly Leu Arg Arg Lys Gly Ser Arg Asp Cys Ser Val Cys
            515                 520                 525

Phe Glu Ser Glu Val Ile Ala Ala Leu Val Pro Cys Gly His Asn Leu
530                 535                 540

Phe Cys Met Glu Cys Ala Asn Arg Ile Cys Glu Lys Ser Glu Pro Glu
545                 550                 555                 560

Cys Pro Val Cys His Thr Ala Val Thr Gln Ala Ile Arg Ile Phe Ser
            565                 570                 575

<210> SEQ ID NO 6
<211> LENGTH: 30
<212> TYPE: DNA
<213> ORGANISM: Artificial Sequence
<220> FEATURE:
<223> OTHER INFORMATION: MEX3B primer Fw1

<400> SEQUENCE: 6
cgtcgtcctc tgtggtcttt cccgggggtg                                30

<210> SEQ ID NO 7
<211> LENGTH: 30
<212> TYPE: DNA
<213> ORGANISM: Artificial Sequence
<220> FEATURE:
<223> OTHER INFORMATION: MEX3B primer Rv1

<400> SEQUENCE: 7
tcaggaaaaa atgcggatgg cctgagtgac                                30

<210> SEQ ID NO 8
<211> LENGTH: 20
<212> TYPE: DNA
<213> ORGANISM: Artificial Sequence
<220> FEATURE:
<223> OTHER INFORMATION: Mouse GAPDH primer Fw1

<400> SEQUENCE: 8
agagacagcc gcatcttctt                                           20

<210> SEQ ID NO 9
<211> LENGTH: 20
<212> TYPE: DNA
<213> ORGANISM: Artificial Sequence
<220> FEATURE:
<223> OTHER INFORMATION: Mouse GAPDH primer Rv1
```

<400> SEQUENCE: 9
gacaagcttc ccattctcgg    20

<210> SEQ ID NO 10
<211> LENGTH: 4368
<212> TYPE: DNA
<213> ORGANISM: Human

<400> SEQUENCE: 10

| | | |
|---|---|---|
| tcaagaggcg gggaggagag gaggaaaaag cgctgagtga gggcgggcgg gcgggcggga | 60 |
| gggagggagt ggaggagccg gggaggggct ccttaaagaa acgcttctgt cgctcgcctg | 120 |
| ctcgcttttc gctcggcatt gcggccagcc agccgggcac tcgggggggca cgcgcggcca | 180 |
| ccgctagagc tctgccccca ccccaccccgc cagcaggtct ggggtgggga cccaggtggg | 240 |
| ggctcctgca gccactgccc ggtgcggacc gcacggagcg acccactcct cccagcaccg | 300 |
| aggaagaagc aacggagccc tcagcaggcg accggcctcc ccgcccctga ccacccgctt | 360 |
| cccggctgcc tttgtggccg cagcttctcg ccgccgagcc gagggccggc ggggggcgcgg | 420 |
| cgcgcacggc cgagcgatgc ccagctcgct gttcgcagac ctggagcgca acggcagcgg | 480 |
| cggcggcggc ggcggcagca gcggaggggg agagaccctg gatgaccaaa gagccctgca | 540 |
| gctcgcgctc gaccagctct ccctgctggg gctggacagt gacgagggcg cctctctgta | 600 |
| cgacagcgag ccgcgcaaga gagcgtgaa catgaccgag tgcgtgccag tacccagttc | 660 |
| tgagcatgtc gccgagatcg tggggcggca aggtaggtcg aggagggatg gggaggtggg | 720 |
| tggggggtggt gtagggtctc aggccactgc ctcgagggga aggcgtgttc agtatcggga | 780 |
| tccgcggcgt ggggtgcctt ggggagagag gaagagccgc gcgatgggcc ggcgccccag | 840 |
| acaaagaaag tgcaggcagg ctgtctcccg gagccgcgcc gctgcctgg cgggatgcac | 900 |
| tttcttctgc taaaatcact gccttctccc ctaacgcccc ccaaccagcc cacctccaga | 960 |
| aagacaattt aaatgtaaga tgcttggggg aggggccttt gatcagtcc tttgggagga | 1020 |
| ggaaggagga ggagtgagca taggatggga ggaggattct ggatttctgc aaagcggaat | 1080 |
| ggagcccaga ggaggaacaa tgggtcccgg gactcacacc ccaccccta cccccagtcg | 1140 |
| accagcgctg aggcatcgcg acttcagctg ccttccccga gccccttccc cgtgtcttca | 1200 |
| gagctgacgg cgcgcccagc tggatcccag cggcatctcc ccagatgact tttctgggat | 1260 |
| tctcgggttt ggttcgggac gactgcagtc actggggggag ggccaggcag ccaatgggct | 1320 |
| gttcctcgag cgcctcgcgg gtgggatccg ctgcccagcc cgtggcgcgg cccgaggtca | 1380 |
| gtgagggaga cgccccctttt ccgcccatct cttgtcctgc cgtctcgctg tcctggacgc | 1440 |
| gggctgtccc cggtccccgc ggttacccca ggataatggg cgtgtctgtc tctctctccc | 1500 |
| actccctcct ccgcaccctg gttcgtaggt tgtaaaatca aagcgctgcg ggcgaagacc | 1560 |
| aatacttaca tcaagacccc agttcgcggg gaggagcctg tctttgttgt gacgggcagg | 1620 |
| aaggaggatg tggccatggc tcggagggag atcatctctg ctgccgagca cttctccatg | 1680 |
| atccgcgcct cccggaataa gaacacggca ctcaacggcg cggtgcctgg gccgcccaac | 1740 |
| ctgccccggggc agaccaccat ccaagtgcgg gtacctacc gcgtggtggg gctcgtggtg | 1800 |
| gggcccaaag gcgccacaat caagcgcatc cagcagcaga cgcacacgta catcgtgacg | 1860 |
| cccagccgga taaggagcc ggtgttcgag gtgaccggca tgccagagaa cgtggatcgc | 1920 |
| gctcgagagg agattgaggc gcacattgct ctgcgtaccg gcggcatcat tgagctcaca | 1980 |

-continued

```
gacgagaacg acttccacgc caacggcacc gatgtgggct tcgatctgca tcatgggtcc    2040
ggcgggtccg gcccaggcag cctctggagc aagcccaccc ccagcatcac gcccaccccc    2100
ggccgcaagc ctttctctag ctaccgcaac gacagctcca gctcgcttgg cagtgcttcc    2160
acagactctt atttcggcgg cgggaccagc agcagcgcag cggctaccca gcgcctggcg    2220
gactacagcc cccctagccc cgccctgagc tttgcgcaca acggaaacaa taacaataac    2280
ggcaatgggt acacctacac agcgggggga gaagcctcag tgccatcccc cgacggctgc    2340
cccgagctgc agcccacttt tgacccggct cccgctcccc cacctggggc accacttatc    2400
tgggcccagt cgagcggtc cccgggaggc ggacctgcag ctccggtatc ttcttcctgc     2460
tcttcttctg catcttcgtc tgcttcttcc tcctccgtgg tcttcccgg gggtggcgcc     2520 agtgcgccct ccaacgccaa cctggggcta ttggtgcacc gccggctgca ccctggcacc    2580
agctgcccgc gcctgtctcc acccttgcac atggccccgg gggcgggaga gcaccacctg    2640
gctcgccggg tgcgcagcga cccggtgga ggaggcctgg cctacgccgc ttatgccaac     2700
gggctggggg cacagctgcc tggcttgcag ccgtcggaca cgtcgggctc ctcctcttcg    2760
tccagctcct cctccagctc ttcatcctct tcctccgggc ttcggcgtaa aggcagccgc    2820
gactgctccg tgtgcttcga gagcgaagtg attgccgcgc tggtgccctg tggccacaac    2880
ctcttctgca tggagtgcgc caatcgcatc tgtgagaaga gcgagcccga gtgcccggtc    2940
tgccacaccg cggtcactca ggccatccgc atcttttctt aaaggcagcg ggcgctgcta    3000
gtgcgcaccg tgctggggga agggggaacc cctccccacc ctctttcccc agcgctcgcc    3060
tgcctccctg ggtgccccc ctctcccttc tccttcccgg ccccaccaac actctgagat     3120
ccgagaggag cttggaaagc tgtagtatcc gctcattttt aaaatttaat ttttaagtaa    3180
aggaatttgc caggatatct gcatcaagag tactgtagcc tgggaaacct gaacacctga    3240
aatgcatgct ctataaataa taggaacggc gacattctag taatgatagt ttttacactg    3300
tacttaatag gaagcttcca aaagaagaaa accccacaag ttttccattt tcttaaagta    3360
ggaaaaaatg aacagtaata attatgatga agatgatagt agtgctatgg gatgtgtgga    3420
ctgtttagtg tgttcccctt tgtgggtggg ttcctatgat acttattata gaacacagtg    3480
gatccttttt gaatgttcgt ggaagggcca ggagttcctg tgaaaccagg atactgcagc    3540
tttattaaag ttaagaaac tgtaacatat ctcttatata ttaaaaacgt ttaaaagttt      3600
taaagagaaa ttgcattaat acagattgaa gtattttatt ctttttgac ttgaaaaatt     3660 atatttcata ttgcaaagat gtttacaagt attttaattt aagttcagtg aacttttttg    3720
tagctgggtt aaatcttttt attttagtat ggccttatgg caaagaacac tgtattattt    3780
taataatcac acaattgtga cggaattaca accataaaat gtgtaatgtt ttgaacagta    3840
ttctgttggg atggagattt tataggttca gacaaatctt ctagatctgc ttcacccagc    3900
atattttcta ttcagtgata taaagcatat tttattctat attattacaa aaacggaaat    3960
gtataaacat gtcaaaaga actgttgatg ctttctaaca tttgtataaa tagaattcag     4020
tgcaagttac aaaaattctg ttgcaccact ctagttttag tatttctatt ttaatacatt    4080
tgtttaccac ttgtttatgt atatgtaggt gatgttactt gagcttaaat gtactttact    4140
gagcaaagtt taaaaaacaa agtatatttt attttatgat aaagggcctt taacctcatg    4200
gtcaaatact aatattatat ttgctgagac aagatttgaa attgtatcaa gagtttttatt   4260 tttctgacat ttaaagttct acataataaa ggtaaaactt aagtaatggt gctacttcat    4320
tttttaagta tttctatata aataaaatat tgaagaaaat cttaaaaa                 4368
```

```
<210> SEQ ID NO 11
<211> LENGTH: 16
<212> TYPE: DNA
<213> ORGANISM: Artificial Sequence
<220> FEATURE:
<223> OTHER INFORMATION: hmrGD-176

<400> SEQUENCE: 11
gtacatttaa gctcaa                                                    16

<210> SEQ ID NO 12
<211> LENGTH: 16
<212> TYPE: DNA
<213> ORGANISM: Artificial Sequence
<220> FEATURE:
<223> OTHER INFORMATION: hmrGD-178

<400> SEQUENCE: 12
gctcagtaaa gtacat                                                    16

<210> SEQ ID NO 13
<211> LENGTH: 16
<212> TYPE: DNA
<213> ORGANISM: Artificial Sequence
<220> FEATURE:
<223> OTHER INFORMATION: hmrGD-179

<400> SEQUENCE: 13
actttgctca gtaaag                                                    16

<210> SEQ ID NO 14
<211> LENGTH: 16
<212> TYPE: DNA
<213> ORGANISM: Artificial Sequence
<220> FEATURE:
<223> OTHER INFORMATION: hmrGD-180

<400> SEQUENCE: 14
tttaaacttt gctcag                                                    16

<210> SEQ ID NO 15
<211> LENGTH: 16
<212> TYPE: DNA
<213> ORGANISM: Artificial Sequence
<220> FEATURE:
<223> OTHER INFORMATION: hmrGD-182

<400> SEQUENCE: 15
cataaaataa aatata                                                    16

<210> SEQ ID NO 16
<211> LENGTH: 16
<212> TYPE: DNA
<213> ORGANISM: Artificial Sequence
<220> FEATURE:
<223> OTHER INFORMATION: hmrGD-199

<400> SEQUENCE: 16
aaaaataaaa ctcttg                                                    16

<210> SEQ ID NO 17
<211> LENGTH: 16
<212> TYPE: DNA
<213> ORGANISM: Artificial Sequence
<220> FEATURE:
```

<223> OTHER INFORMATION: hmrGD-201

<400> SEQUENCE: 17
taaatgtcag aaaaat                                                         16

<210> SEQ ID NO 18
<211> LENGTH: 16
<212> TYPE: DNA
<213> ORGANISM: Artificial Sequence
<220> FEATURE:
<223> OTHER INFORMATION: hmrGD-202

<400> SEQUENCE: 18
aactttaaat gtcaga                                                         16

<210> SEQ ID NO 19
<211> LENGTH: 16
<212> TYPE: DNA
<213> ORGANISM: Artificial Sequence
<220> FEATURE:
<223> OTHER INFORMATION: hmrGD-203

<400> SEQUENCE: 19
tgtagaactt taaatg                                                         16

<210> SEQ ID NO 20
<211> LENGTH: 16
<212> TYPE: DNA
<213> ORGANISM: Artificial Sequence
<220> FEATURE:
<223> OTHER INFORMATION: hmrGD-205

<400> SEQUENCE: 20
acctttatta tgtaga                                                         16

<210> SEQ ID NO 21
<211> LENGTH: 15
<212> TYPE: DNA
<213> ORGANISM: Artificial Sequence
<220> FEATURE:
<223> OTHER INFORMATION: control

<400> SEQUENCE: 21
aacacgtcta tacgc                                                          15

<210> SEQ ID NO 22
<211> LENGTH: 16
<212> TYPE: DNA
<213> ORGANISM: Artificial Sequence
<220> FEATURE:
<223> OTHER INFORMATION: hmrGD-68

<400> SEQUENCE: 22
gcgggcagct ggtgcc                                                         16

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
acccagttct gagcatgtcg                                                     20

```
<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24 cgaactggggg tcttgatgta a                                             21

<210> SEQ ID NO 25
<211> LENGTH: 20
<212> TYPE: DNA
<213> ORGANISM: Artificial Sequence
<220> FEATURE:
<223> OTHER INFORMATION: GAPDH primer 2 F

<400> SEQUENCE: 25
gcaccgtcaa ggctgagaac                                                20

<210> SEQ ID NO 26
<211> LENGTH: 19
<212> TYPE: DNA
<213> ORGANISM: Artificial Sequence
<220> FEATURE:
<223> OTHER INFORMATION: Human GAPDH primer 2 Reverse

<400> SEQUENCE: 26
tggtgaagac gccagtgga                                                 19
```

NUCLEIC ACID INHIBITING EXPRESSION OF THE MEX3B GENE, MEX3B GENE EXPRESSION INHIBITOR, METHOD FOR INHIBITING MEX3B GENE EXPRESSION, AND PROPHYLACTIC OR THERAPEUTIC AGENT FOR DISEASE CAUSED BY MEX3B GENE EXPRESSION

TECHNICAL FIELD

The present invention relates to a nucleic acid which inhibits expression of MEX3B gene, an MEX3B gene expression inhibitor containing the nucleic acid, a method for inhibiting expression of the MEX3B gene, and a prophylactic or therapeutic agent for a disease caused by expression of the MEX3B gene.

BACKGROUND ART

The MEX3B gene has been originally identified as a gene activated by TGF-β, and, according to the analyses thereafter, the MEX3B protein was known as a molecule which binds to various types of mRNA and controls the function of those mRNAs (i.e., translation into protein) (e.g., Non-Patent Document 1).

Furthermore, it is also known that the MEX3B protein is a protein which induces apoptosis (e.g., Patent Document 1).

It is known that apoptosis is involved in, other than a normal physiological process, an onset of serious disorder such as neurodegenerative disorder. For example, it is considered that a neurodegenerative disorder (e.g., Alzheimer's disease, Parkinson's disease, amyotrophic lateral sclerosis, Huntington's disease, and the like) is caused by abnormally increased apoptosis (e.g., Non-Patent Document 2).

Patent Document 1: Japanese Patent No. 4429269
Non-Patent Document 1: Nucleic Acids Res. 2007; 35(4): 1289-300.
Non-Patent Document 2: Wolozin, B., et al., (1996) Science, 274, 1710-1713

DISCLOSURE OF THE INVENTION

Problems to be Solved by the Invention

Under the above background, development of a medicinal product of a nucleic acid for inhibiting the expression of the MEX3B gene while suppressing a side effect has been required.

The present invention is achieved in consideration of the above circumstances, and an object of the invention is to provide a nucleic acid which has low cytotoxicity as a side effect and can inhibit expression of the MEX3B gene, an MEX3B gene expression inhibitor containing the nucleic acid, a method for inhibiting expression of the MEX3B gene, and a prophylactic or therapeutic agent for a disease caused by expression of the MEX3B gene.

Means for Solving the Problems

Inventors of the present invention found that, when mRNA expression of the MEX3B gene is inhibited by using an antisense oligonucleotide having a sequence complementary to an oligonucleotide contained in an amino acid-coding region (CDS) in an exon of the MEX3B gene, cell cytotoxicity is easily shown.

On the other hand, it was also surprisingly found that, when an antisense oligonucleotide having a sequence complementary to an oligonucleotide contained in an untranslated region (UTR) in an exon, which does not encode any amino acid, is used, cell cytotoxicity as a side effect is low and mRNA expression of the MEX3B gene is inhibited.

It is believed that the low level of cytotoxicity as a side effect is due to the fact that, compared to CDS, UTR has lower homology with MEX3B homologs and is less likely to have an occurrence of the off-target effect.

The present invention has been completed based on the above findings.

Specifically, the present invention is as those described below.

The first embodiment of the present invention is a nucleic acid inhibiting expression of MEX3B gene which is an antisense oligonucleotide having a sequence complementary to an oligonucleotide that comprises at least 10 contiguous nucleotides in an untranslated region in an exon of the MEX3B gene, or a double-stranded RNA containing at least 20 contiguous nucleotides in the untranslated region or a DNA encoding the double-stranded RNA.

The second embodiment of the present invention is an MEX3B gene expression inhibitor comprising the nucleic acid according to the first embodiment.

The third embodiment of the present invention is a method for inhibiting expression of MEX3B gene comprising contacting a subject (excluding human individual) with the agent according to the second embodiment.

The fourth embodiment of the present invention is a prophylactic or therapeutic agent for a disease caused by expression of MEX3B gene containing the agent according to the second embodiment.

Effects of the Invention

A nucleic acid which has low cytotoxicity as a side effect and can inhibit expression of the MEX3B gene, an MEX3B gene expression inhibitor containing the nucleic acid, a method for inhibiting the expression of the MEX3B gene, and a prophylactic or therapeutic agent for a disease caused by the expression of the MEX3B gene can be provided.

PREFERRED MODE FOR CARRYING OUT THE INVENTION

Figure 1:
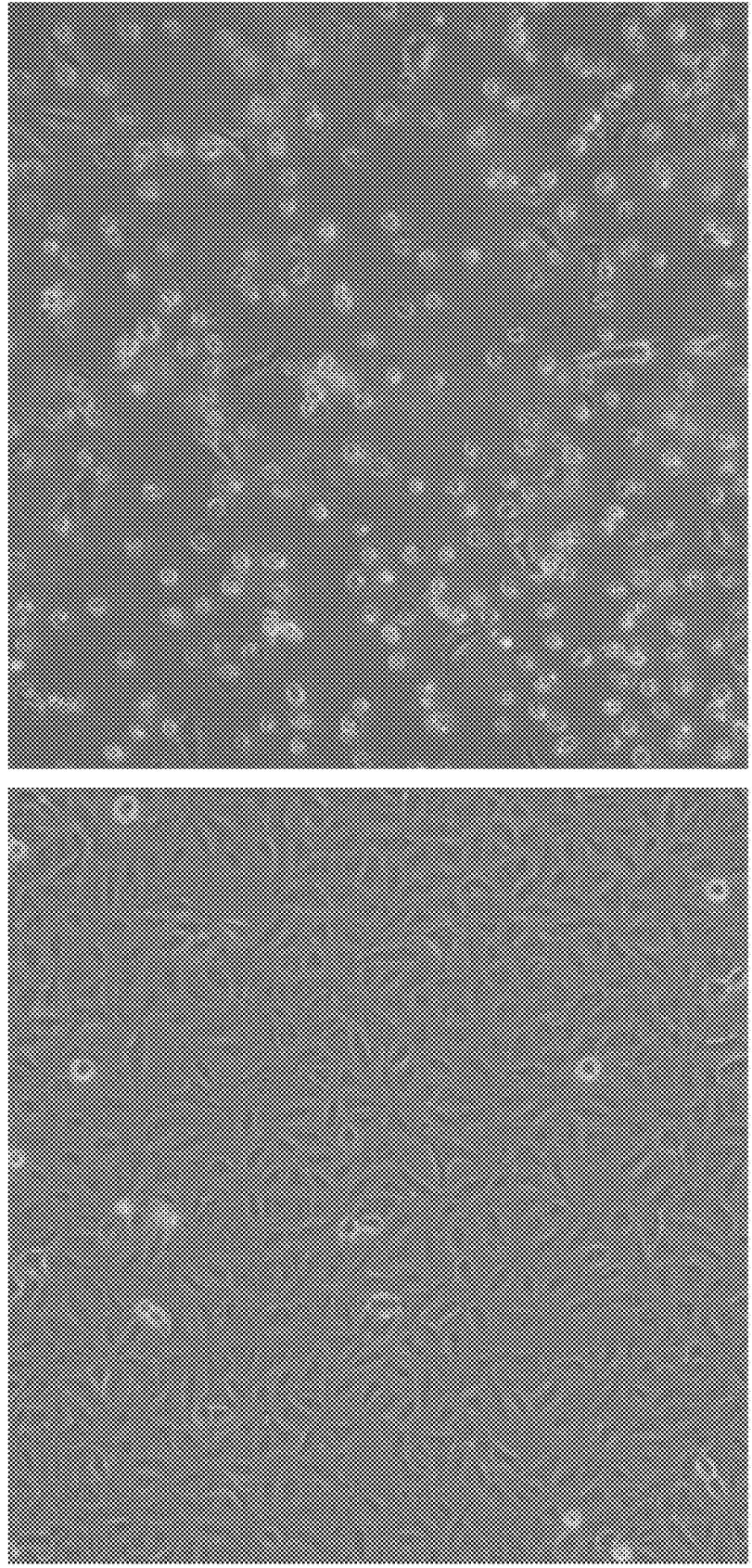
FIG. 1(a) is a view showing a microscopic image of cells having no cytotoxicity due to the use of a gapmer type nucleic acid (manufactured by Takara Bio Inc.) as a negative control that does not inhibit the MEX3B.
FIG. 1(b) is a view showing a microscopic image of cells having cytotoxicity caused by a gapmer type nucleic acid of Comparative Example.

Hereinbelow, embodiments of the present invention are described in detail, but, the present invention is not at all limited to the following embodiments, and it can be carried out with suitable modifications within the range of the purpose of the present invention.

(MEX3B Gene)

The MEX3B gene includes exon 1, intron, and exon 2, and this constitution is highly conserved in human, mouse, and other mammals. As an untranslated region (UTR) in an exon which does not encode any amino acid, 5'UTR is present upstream of the initiation codon and 3'UTR is present downstream of the termination codon.

Human MEX3B gene encoding the mRNA of human MEX3B has a sequence represented by SEQ ID NO: 1 that is described later.

In SEQ ID NO: 1, the sequence from 437 to 2146 positions corresponds to CDS, the sequence from 1 to 436 positions corresponds to 5'UTR, and the sequence from 2147 to 3532 positions corresponds to 3'UTR.

Mouse MEX3B gene encoding the mRNA of mouse MEX3B has a sequence represented by SEQ ID NO: 2 that is described later.

In SEQ ID NO: 2, the sequence from 319 to 2049 positions corresponds to CDS, the sequence from 1 to 318 positions corresponds to 5'UTR, and the sequence from 2050 to 3416 positions corresponds to 3'UTR.

SEQ ID NO: 3 described later represents 836 bases in an intron region of the human MEX3B gene.

SEQ ID NO: 10 represents the sequence encoding a pre-mRNA of the human MEX3B before splicing.

In the sequence encoding a pre-mRNA of the human MEX3B that is represented by SEQ ID NO: 10, the sequences from 437 to 692 positions and 1529 to 2982 positions correspond to CDS, the sequence from 1 to 436 positions corresponds to 5'UTR, the sequence from 2983 to 4368 positions corresponds to 3'UTR, and the region from 693 to 1528 positions corresponds to the intron region of the human MEX3B gene that is represented by SEQ ID NO: 3.

Furthermore, all genes encoding the MEX3B protein (e.g., protein having an amino acid sequence represented by SEQ ID NO: 4 or 5 that is described later) belong to the MEX3B gene.

(Obtainment of MEX3B Gene)

Method for obtaining the MEX3B gene is not particularly limited. By preparing a suitable probe or primer based on the information of the nucleotide sequence and amino acid sequence that are described in SEQ ID NOs: 1, 2, 4, 5, and 10 of the Sequence Listing of the present specification and selecting a desired clone from human cDNA library (i.e., prepared by a common method using suitable cells in which the MEX3B gene is expressed) by using them, the MEX3B gene can be isolated.

<Nucleic Acid Inhibiting Expression of MEX3B Gene>

The nucleic acid inhibiting the expression of the MEX3B gene according to the first embodiment (hereinbelow, also simply referred to as a "nucleic acid according to the first embodiment) is an antisense oligonucleotide having a sequence complementary to an oligonucleotide that contains at least 10 contiguous nucleotides in an untranslated region (UTR) in an exon of the MEX3B gene, or a double-stranded RNA containing at least 20 contiguous nucleotides in the UTR or a DNA encoding the double-stranded RNA.

(Antisense Oligonucleotide)

One embodiment of the nucleic acid according to the first embodiment is an antisense oligonucleotide having a sequence complementary to an oligonucleotide that contains at least 10 contiguous nucleotides in an UTR in an exon of the MEX3B gene.

For example, it is preferable that an oligonucleotide contained in an UTR in an exon of the MEX3B gene and an antisense oligonucleotide complementary thereto form a hybrid after introduction to cells so that mRNA of the MEX3B containing the nucleotide strand is degraded by a nuclease specific to the generated hybrid double strand (e.g., RNase H).

The antisense oligonucleotide may be either a DNA or an RNA, but, from the viewpoint of forming a hybrid with an oligonucleotide contained in an UTR in an exon, it is preferably a DNA.

The UTR in which an oligonucleotide containing at least 10 contiguous nucleotides having a sequence complementary to the antisense oligonucleotide is present may be either 5'UTR or 3'UTR, but, from the viewpoint of having low cytotoxicity, it is preferably 3'UTR.

The antisense oligonucleotide is preferably an antisense oligonucleotide having a sequence complementary to an oligonucleotide that contains at least 11 contiguous nucleotides in the sequence (UTR in an exon) of the MEX3B gene, it is more preferably an antisense oligonucleotide having a sequence complementary to an oligonucleotide that contains at least 12 nucleotides, it is even more preferably an antisense oligonucleotide having a sequence complementary to an oligonucleotide that contains at least 13 nucleotides, and it is particularly preferably an antisense oligonucleotide having a sequence complementary to an oligonucleotide that contains at least 14 nucleotides.

Furthermore, with regard to the upper limit value of the nucleotide length of the antisense oligonucleotide, an antisense oligonucleotide having a sequence complementary to an oligonucleotide with 40 or less contiguous nucleotides in the sequence (UTR in an exon) of the MEX3B gene is preferable, an antisense oligonucleotide having a sequence complementary to an oligonucleotide with 30 or less contiguous nucleotides is more preferable, an antisense oligonucleotide having a sequence complementary to an oligonucleotide with 25 or less contiguous nucleotides is even more preferable, an antisense oligonucleotide having a sequence complementary to an oligonucleotide with 20 or less contiguous nucleotides is particularly preferable, and an antisense oligonucleotide having a sequence complementary to an oligonucleotide with 17 or less contiguous nucleotides is most preferable.

Examples of the antisense oligonucleotide include an antisense oligonucleotide which has a sequence complementary to an oligonucleotide containing 12 to 20 contiguous nucleotides in an UTR, and an antisense oligonucleotide which has a sequence complementary to an oligonucleotide containing 12 to 20 contiguous nucleotides in the sequence from 4119 to 4293 positions of SEQ ID NO: 10, which represents a pre-mRNA of the human MEX3B, or an antisense oligonucleotide which has a sequence complementary to an oligonucleotide from 3135 to 3149 positions in an UTR of SEQ ID NO: 2, which represents the mouse MEX3B gene, is preferable, an antisense oligonucleotide which has a sequence complementary to an oligonucleotide from 4119 to 4134 positions, an oligonucleotide from 4129 to 4144 positions, an oligonucleotide from 4134 to 4149 positions, an oligonucleotide from 4139 to 4154 positions, an oligonucleotide from 4163 to 4178 positions, an oligonucleotide from 4248 to 4263 positions, an oligonucleotide from 4258 to 4273 positions, an oligonucleotide from 4263 to 4278 positions, an oligonucleotide from 4268 to 4283 positions, or an oligonucleotide from 4278 to 4293 positions of SEQ ID NO: 10, which represents a pre-mRNA of the human MEX3B, or an antisense oligonucleotide which has a sequence complementary to an oligonucleotide from 3135 to 3149 positions in an UTR of SEQ ID NO: 2, which represents the mouse MEX3B gene, is more preferable, and an antisense oligonucleotide which has a sequence complementary to an oligonucleotide from 4134 to 4149 positions, an oligonucleotide from 4139 to 4154 positions, or an oligonucleotide from 4278 to 4293 positions of SEQ ID NO: 10, which represents a pre-mRNA of the human MEX3B, is even more preferable.

The antisense oligonucleotide is preferably an antisense oligonucleotide which contains at least one nucleotide having at least one structure that is selected from the group consisting of a phosphorothioate structure, a bridged structure, and an alkoxy structure.

For example, as the phosphodiester bonding part connecting nucleotides has a phosphorothioate structure, resistance to nuclease can be obtained, and, from the viewpoint that the hydrophobicity is enhanced, enhanced incorporation to inside of a cell or a nucleus can be also obtained.

Furthermore, as the sugar part of a nucleotide has a bridged structure such as 2',4'-BNA (2',4'-Bridged Nucleic Acid; other name—Locked Nucleic Acid (LNA)) and ENA (2'-O,4'-C-Ethylene-bridged Nucleic Acid), or an alkoxy structure such as 2'-O-methylaion and 2'-O-methoxyethylation (2'-M0E), the resistance to nuclease can be obtained and also binding property of mRNA can be enhanced.

With regard to the antisense oligonucleotide, it is preferable that at least one phosphodiester bonding part connecting nucleotides has a phosphorothioate structure, it is more preferable that 50% or more of the phosphodiester bond in the antisense oligonucleotide has a phosphorothioate structure, it is even more preferable that 70% or more of the phosphodiester bond in the antisense oligonucleotide has a phosphorothioate structure, it is particularly preferable that 90% or more of the phosphodiester bond in the antisense oligonucleotide has a phosphorothioate structure, and it is most preferable that all of the phosphodiester bonds in the antisense oligonucleotide have a phosphorothioate structure.

With regard to the antisense oligonucleotide, it is preferable that at least any one terminal nucleotide has a bridged structure or an alkoxy structure, it is more preferable that the nucleotides at both terminals of the antisense oligonucleotide have a bridged structure or an alkoxy structure (i.e., so-called gapmer type antisense oligonucleotide), it is even more preferable that, in both terminals of the antisense oligonucleotide, up to 4 bases from the terminal independently have a bridged structure or an alkoxy structure, and it is particularly preferable that 2 or 3 bases from the terminal have a bridged structure or an alkoxy structure.
(siRNA)

Another embodiment of the nucleic acid according to the first embodiment is a double-stranded RNA (small interfering RNA (siRNA)) containing at least 20 contiguous nucleotides in an UTR of the sequence of an RNA to be transcribed from the sequence of the MEX3B gene, or a DNA encoding the double-stranded RNA.

The UTR in which at least 20 contiguous nucleotides included in the double-stranded RNA are present may be either 5'UTR or 3'UTR, but it is preferably 3'UTR.

A double-stranded RNA containing at least 21 contiguous nucleotides in an UTR of the sequence of an RNA to be transcribed from the sequence of the MEX3B gene, or a DNA encoding that double-stranded RNA is preferable.

A double-stranded RNA containing 30 or less contiguous nucleotides in an UTR of the sequence of an RNA to be transcribed from the sequence of the MEX3B gene, or a DNA encoding that double-stranded RNA is preferable, and a double-stranded RNA containing 25 or less contiguous nucleotides in an UTR of the sequence of an RNA to be transcribed from the sequence of the MEX3B gene, or a DNA encoding that double-stranded RNA is more preferable.

Examples of the double-stranded RNA or the DNA encoding the double-stranded RNA include a double-stranded RNA containing at least 21 contiguous nucleotides from 4119 to 4293 positions in an UTR of SEQ ID NO: 10, which represents a pre-mRNA of the human MEX3B, or a DNA encoding that double-stranded RNA, a double-stranded RNA containing an oligonucleotide from 3135 to 3149 positions in an UTR of SEQ ID NO: 2, which represents the mouse MEX3B gene, or a DNA encoding that double-stranded RNA, and a double-stranded RNA containing an oligonucleotide from 4119 to 4134 positions, an oligonucleotide from 4129 to 4144 positions, an oligonucleotide from 4134 to 4149 positions, an oligonucleotide from 4139 to 4154 positions, an oligonucleotide from 4163 to 4178 positions, an oligonucleotide from 4248 to 4263 positions, an oligonucleotide from 4258 to 4273 positions, an oligonucleotide from 4263 to 4278 positions, an oligonucleotide from 4268 to 4283 positions, or an oligonucleotide from 4278 to 4293 positions in an UTR of SEQ ID NO: 10, which represents a pre-mRNA of the human MEX3B, or a DNA encoding that double-stranded RNA, or a double-stranded RNA containing an oligonucleotide from 3135 to 3149 positions in an UTR of SEQ ID NO: 2, which represents the mouse MEX3B gene, or a DNA encoding that double-stranded RNA is preferable.

RNA interference (RNAi) indicates a phenomenon showing inhibited expression of a target gene when an RNA (double-stranded RNA: dsRNA) in which part of mRNA encoding a part of a certain target gene is prepared as a double strand is introduced to cells.

Examples of a DNA encoding a double-stranded RNA include a DNA having a reverse-direction repeating sequence of a partial sequence of the MEX3B.

By introducing a DNA having such a reverse-direction repeating sequence to cells of mammals, the reverse-direction repeating sequence of a target gene (MEX3B) can be expressed in cells, and, accordingly, it becomes possible to inhibit the expression of the target gene (MEX3B) based on the RNAi effect.

The reverse-direction repeating sequence indicates a sequence in which a target gene and a sequence in the reverse reaction thereof are present in parallel via a suitable sequence.

Specifically, for a case in which a target gene has a double-strand consisting of n nucleotide sequences shown below, 5'-$X_1 X_2 \ldots X_{n-1} X_n$-3'
3'-$Y_1 Y_2 \ldots Y_{n-1} Y_n$-5' the reverse-direction sequence thereof has a sequence shown below.

5'-$Y_n Y_{n-1} \ldots Y_2 Y_1$-3'
3'-$X_n X_{n-1} \ldots X_2 X_1$-5'

(herein, with regard to the bases represented by X and the bases represented by Y, those having the same subscript are the bases that are complementary to each other).

The reverse-direction repeating sequence is a sequence in which the above two types of sequence are present via a suitable sequence. As the reverse-direction repeating sequence, a sequence having a target gene upstream of the reverse-direction sequence and a sequence having a reverse-direction sequence upstream of a target gene sequence are considered.

The reverse-direction repeating sequence used in the present invention can be any one of them, but it is preferable that the reverse-direction sequence is present upstream of a target gene sequence.

The sequence present between a target gene sequence and a reverse-direction sequence thereof is a region in which a hairpin loop is formed when transcription into an RNA is made (shRNA: small hairpin RNA). Length of this region is not particularly limited as long as a hairpin loop can be formed, but it is preferable to be approximately 0 to 300 bp, and more preferable to be approximately 0 to 100 bp. It is also possible that a restriction enzyme site is present in that sequence.

According to the present invention, by incorporating a reverse-direction repeating sequence of a target gene to a downstream of a sequence of a promoter which is operable in mammals, the reverse-direction repeating sequence of a target gene can be expressed in cells of mammals. A sequence of a promoter used in the present invention is not particularly limited as long as it is operable in mammals.

The nucleic acid according to the first embodiment can be produced by a common method by using a DNA synthesizer and a known technique for organic synthesis.

Incorporation to a cell, either in vivo or in vitro, can be achieved by contacting a cell with the nucleic acid according to the first embodiment, for example, by adding the nucleic acid according to the first embodiment to a medium in which arbitrary cells are cultured. However, as the nucleic acid according to the first embodiment has at least one structure that is selected from the group consisting of a phosphorothioate structure, a bridged structure, and an alkoxy structure, incorporation to a cell can be further enhanced.

As the nucleic acid according to the first embodiment has at least one structure that is selected from the group consisting of a phosphorothioate structure, a bridged structure, and an alkoxy structure and is used in combination with a carrier for lipofection that is described later, incorporation to a cell can be further enhanced.

The method for introducing a nucleic acid according to the first embodiment to cells can be a method in which insertion to a suitable vector is made and further introduction to a suitable host cells is carried out.

Type of the suitable vector is not particularly limited, and it can be a self-replicating vector (e.g., plasmid or the like), for example. However, it is preferably a vector that is incorporated into a genome of a host cell upon introduction to a host cell and replicated with an incorporated chromosome. As the suitable vector, a plasmid derived from *E. coli* (e.g., pBR322, pUC118, and the like), a plasmid derived from *Bacillus subtilis* (e.g., pUB110, pSH19, and the like), and also bacteriophage, an animal virus such as retrovirus or vaccinia virus, or the like can be used. During recombination, it is also possible to add a translation initiation codon or a translation termination codon by using a suitable synthetic DNA adaptor.

Furthermore, if necessary, the nucleic acid according to the first embodiment can be also functionally bound to a suitable terminator such as a human growth hormone terminator, or, for a fungal host, a TPI1 terminator or an ADH3 terminator, for example. The recombination vector may also have an element such as polyadenylation signal (e.g., those derived from SV40 or adenovirus 5E1b region), a transcription enhancer sequence (e.g., SV40 enhancer), and a translation enhancer sequence (e.g., those encoding adenovirus VARNA).

The recombination vector may also be provided with a DNA sequence which enables replication of the vector in a host cell, and examples thereof include SV40 replication origin (when host cell is a mammalian cell).

The recombination vector may also include a selection marker. Examples of the selection marker include a gene that does not have complement in a host cell such as dihydrofolate reductase (DHFR) or *Schizosaccharomyces pombe* TPI gene, or a gene resistant to pharmaceuticals such as ampicillin, kanamycin, tetracycline, chloramphenicol, neomycin, or hygromycin, for example.

Examples of a host cell to which the nucleic acid according to the first embodiment or a vector containing the nucleic acid is introduced include a higher eukaryotic cell, a bacterium, a yeast, and a fungus, but it is preferably a mammalian cell.

Examples of the mammalian cells include HEK293 cell, HeLa cell, COS cell (e.g., COS-7 cell and the like), BHK cell, CHL cell or CHO cell, and BALB/c mouse cell (e.g., BALB/c mouse embryonic fibroblast cell). A method of transforming a mammalian cells and expressing a gene introduced to the cells is also known, and a lipofection method, an electroporation method, a calcium phosphate method, and the like can be used, for example.

When the sequence information of the MEX3B gene is used as a base, inhibition of the expression of the MEX3B gene by the nucleic acid according to the first embodiment can be determined, both in vivo and in vitro, by using a probe or a primer which has a partial or whole sequence of the gene.

In particular, measurement of an expression amount of the MEX3B gene at mRNA level can be carried out by a common method such as RT-PCR and Northern blot.

In the case of carrying out PCR, the primers are not particularly limited as long as they can specifically amplify the MEX3B gene only, and they can be suitably set based on the sequence information of the MEX3B gene. For example, an oligonucleotide that contains at least 10 contiguous nucleotides in the MEX3B gene, and an antisense oligonucleotide having a sequence complementary to the oligonucleotide can be used as a probe or a primer. More specifically, an oligonucleotide which has a sequence of 10 to 60 contiguous bases, and preferably 10 to 40 contiguous bases in the MEX3B gene, and an antisense oligonucleotide having a sequence complementary to the oligonucleotide can be used.

Furthermore, measurement of an expression amount at the MEX3B protein level can be carried out by a common immunoassay such as Western blot or ELISA. Specifically, the measurement can be carried out by a common method that is known to a person skilled in the pertinent art such as those described in the second edition of Molecular Cloning, Current Protocols in Molecular Biology, or the like.

<MEX3B Gene Expression Inhibitor>

The MEX3B gene expression inhibitor according to the second embodiment (hereinbelow, also simply referred to as an "agent according to the second embodiment") contains the nucleic acid according to the first embodiment.

The MEX3B gene expression inhibitor according to the second embodiment may additionally contain a carrier for lipofection from the viewpoint of enhancing the incorporation to a cell, but it is also possible not to contain any carrier.

Examples of the carrier for lipofection include a carrier which has high affinity to cell membrane (e.g., liposome, cholesterol, or the like), and it is preferably lipofectamine or lipofectin, and more preferably lipofectamine.

As the nucleic acid according to the first embodiment has at least one structure that is selected from the group consisting of a phosphorothioate structure, a bridged structure, and an alkoxy structure and is used in combination with a carrier for lipofection, incorporation to a cell can be further enhanced.

For example, it is preferable that the nucleic acid according to the first embodiment which has at least one structure that is selected from the group consisting of a phosphorothioate structure, a bridged structure, and an alkoxy structure is brought into contact with a subject which is described later in the presence of a carrier for lipofection.

The agent according to the second embodiment can be also in the form in which the nucleic acid according to the first embodiment, the above carrier for lipofection and other optional component (e.g., water, buffer solution, and the like) are mixedly contained, but it is also possible to have the form of a kit having the nucleic acid according to the first embodiment and other optional component, and the above carrier for lipofection and other optional component are packaged in an individual container.

The form of the agent according to the second embodiment is not particularly limited, but the agent can be used in the form of a liquid, a granule, a tablet, a capsule, a pharmaceutical to be patched, or the like. In the case of in vivo, it is also possible to directly apply the agent according to the second embodiment to a tissue. More preferably, the agent (liquid or the like) is exposed to a living body, or administrated into a living body orally, or by a means such as injection, spray, or coating to inside of a blood vessel such as vein or artery, inside of a mouth, under a tongue, inside of rectum, inside of an abdomen, skin, subcutaneous, intradermal, inside of a bladder, or inside of a respiratory tract (bronchus), an eye, a nose, or an ear.

<Method for Inhibiting MEX3B Gene Expression>

The method for inhibiting expression of the MEX3B gene according to the third embodiment includes contacting a subject with the agent according to the second embodiment.

Examples of the subject include an individual organism, a microorganism, a protozoan, a biological tissue, a biological tissue specimen, a human cell, and an animal cell.

The mode for bringing the subject in contact with the agent is not particularly limited, but it is possible that the agent according to the second embodiment is added to a medium including the subject, or a medium containing in advance the agent according to the second embodiment can be prepared. The temperature, time, or the like at the time of bringing the subject in contact are not particularly limited, and they are suitably set depending on the type of a subject or the like.

<Prophylactic or Therapeutic Agent for Disease Caused by MEX3B Gene Expression>

The prophylactic or therapeutic agent for a disease caused by expression of the MEX3B gene according to the fourth embodiment contains the MEX3B gene expression inhibitor according to the second embodiment.

Interleukin 6 (IL-6) is an important cytokine which is involved in inflammation, hematopoiesis, bone metabolism, tumor aggravation, or the like, and the activity of interleukin 6 (IL-6) is known to contribute mainly to a transition from acute inflammation to acquired immune response or an onset of a chronic inflammatory disorder (e.g., J Asthma. 2008; 45 Suppl 1: 41-4).

As an inflammatory cytokine, interleukin 13 (IL-13) is known to play a role of enhancing allergic inflammation in peripheral tissues, and, in addition to the aspect of promoting an allergy reaction as a main cause of allergic asthma, it is also known to be involved in intractability of asthma for which a steroid agent is ineffective.

Furthermore, IL-13 is involved in forming of a syndrome not only in asthma but also in inflammatory bowel disease and atopic dermatitis (e.g., J Allergy (Cairo). 2012; 2012: 316049, N Engl J Med 2011; 365: 1088-1098).

Tumor Necrosis Factor (TNF), in particular, TNF-α, is a signal factor which induces an inflammatory reaction, and even though it is a factor that is important in terms of a defense against infection, it is also known to be involved simultaneously in a disorder caused by augmented inflammation. Namely, TNF is involved in aggravation of a syndrome in many disorders, and it is known to be involved mainly in a joint disorder (rheumatoid arthritis, psoriatic arthritis, spondyloarthropathy, and ankylosing spondylitis), an inflammatory bowel disease (ulcerative colitis and Crohn's disease), a cancer (ovarian cancer and breast cancer), a mental disorder (depression, bipolar disorder, epilepsy, Alzheimer's disease, Parkinson's disease, and multiple sclerosis), a cardiovascular disorder (heart failure and arteriosclerosis), a respiratory tract disorder (bronchial asthma, chronic bronchitis, chronic obtrusive pulmonary disease, and acute lung injury), type 2 diabetes, a kidney disorder (ischemic renal disorder, rejection after transplantation, and glomerulonephritis), and the like (e.g., J Allergy Clin Immunol. 2008 January; 121 (1): 5-10, J Pathol. 2008 January; 214 (2): 149-60).

Furthermore, Granulocyte-Colony Stimulating Factor (G-CSF) is known to have an activity of promoting granulocyte production and enhancing the function of neutrophils.

Furthermore, IL-13, TNF, and G-CSF are also known to be involved in a progress of asthma (e.g., Curr Opin Immunol. 2013 December; 25 (6): 755-60).

Furthermore, CXCL1, CXCL2, and CXCL5 belong to the inflammatory chemokine CXC subfamily.

When CXCL1, CXCL2, and CXCL5 are secreted in lung tissues due to an augmentation of excessive inflammation in tracheal mucous membrane, infiltration of neutrophils, which express high-level CXCR2 as a receptor of CXCL1, CXCL2, and CXCL5, is promoted. Consequently, as severe asthma is caused by the infiltration of neutrophils which have resistance to steroids, chronic inflammation inducing irreversible tracheal remodeling is caused.

Inventors of the present invention found that the MEX3B gene is related with an onset of a disease that is caused by IL-6, IL-13, TNF, G-CSF, CXCL1, CXCL2, or CXCL5.

Therefore, the prophylactic or therapeutic agent according to the fourth embodiment is considered to be effective as a prophylactic or therapeutic agent for the prevention or treatment of the diseases caused by an increased expression of IL-6, IL-13, TNF, G-CSF, CXCL1, CXCL2, or CXCL5 (e.g., among severe asthma, chronic obtrusive pulmonary disease, rheumatoid arthritis, colitis, Crohn's disease, atopic dermatitis, systemic erythematosus, cancer, or the like, severe asthma, chronic obtrusive pulmonary disease, rheumatoid arthritis, colitis, Crohn's disease, atopic dermatitis, systemic erythematosus, cancer, and the like that are caused by IL-6, IL-13, TNF, G-CSF, CXCL1, CXCL2, or CXCL5 (Int Immunol. 2015 January; 27 (1): 21-9, Cancer Discov. 2016 January; 6 (1): 80-95)).

Furthermore, the MEX3B protein is known as a protein which can induce apoptosis (e.g., Japanese Patent No. 4429269).

Apoptosis is known to be involved in, in addition to normal physiological processes, an onset of a serious disorder like neurodegenerative disorder. For example, a neurodegenerative disorder (e.g., Alzheimer's disease, Parkinson's disease, amyotrophic lateral sclerosis, and Huntington's disease) is considered to be caused by abnormally increased apoptosis (Wolozin, B., et al., (1996) Science, 274, 1710-1713).

Accordingly, the prophylactic or therapeutic agent according to the fourth embodiment is considered to be effective as a prophylactic or therapeutic agent for a neurodegenerative disorder.

The prophylactic or therapeutic agent according to the fourth embodiment can be administered systemically or topically, either orally or parenterally. Examples of a method for parenteral administration include intravenous injection like dropping addition, intramuscular injection, intraperitoneal injection, and subcutaneous injection. The administration method can be suitably selected depending on age and symptom of a patient. The administration amount varies depending on age, administration route, and the number of administrations, and it can be suitably selected by a person who is skilled in the pertinent art. Examples of the preparation form suitable for parenteral administration include those containing additives such as stabilizing agent, buffering agent, preservative, isotonic acid, or the like, and those containing a pharmaceutically acceptable carrier or additional product are also acceptable. Examples of those carrier and additional product include water, an organic solvent, a polymer compound (collagen, polyvinyl alcohol, or the like), stearic acid, human blood serum albumin (HSA), mannitol, sorbitol, lactose, and a surface active agent, but they are not limited thereto.

The administration amount of the nucleic acid according to the first embodiment as an effective component is, for single administration, generally within a range approximately 0.1 µg to 100 mg per kg of bodyweight.

EXAMPLES

Hereinbelow, the present invention is described in greater detail by showing examples, but the scope of the present invention is not limited to those examples.

Example 1

Preparation of Gapmer Type Nucleic Acid

Comparative Example

As a gapmer type nucleic acid of Comparative example, a gapmer type nucleic acid (total length: 16 bases) complementary to the sequence from 838 to 853 positions of SEQ ID NO: 1, which is included in an amino acid-coding region (CDS) in the sequence of the human MEX3B mRNA, was prepared.

Example

As a gapmer type nucleic acid of Example, a gapmer type nucleic acid (total length: 15 bases) complementary to the sequence from 3135 to 3149 positions included in 3'UTR of SEQ ID NO: 2, which represents the mouse Mex3B gene, was prepared.

At both ends of the gapmer type nucleic acid of Comparative example and Example, 2 or 3 bases of LNA (2',4'-BNA) were added and natural DNA was employed as bases filling other gaps while the phosphodiester bond connecting each nucleotide was phosphorothioated.

<Transfection Using Gapmer Type Nucleic Acid>

By using the gapmer type nucleic acid of Comparative Example and the gapmer type nucleic acid of Example, transfection (cell incorporation) was carried out.

Cells used for the transfection with a gapmer type nucleic acid were mouse lung epithelial cells MLE15, and by employing lipofectamine RNAiMax (manufactured by Invitrogen) and the recommended protocol thereof, the nucleic acids were incorporated into cells to achieve final concentration of 20 nM.

<Quantitative RT-PCR Test>

48 hours after the transfection, state of the cells was observed under a microscope, and thereafter, the cells were recovered and the total RNA was recovered by using dissolution buffer-TRIsure (manufactured by BIOLINE). By using Primescript (manufactured by Takara Bio Inc.), a reverse transcription reaction was carried out to obtain cDNA.

After that, by using Light Cycler 480 (manufactured by ROCHE), quantitative RT-PCR was carried out.

Sequence of the primer used for the quantitative RT-PCR test was as follows.

```
Mouse MEX3B primer Forward:
                                        (SEQ ID NO: 6)
5'-CGTCGTCCTCTGTGGTCTTTCCCGGGGGTG-3'

Mouse MEX3B primer Reverse:
                                        (SEQ ID NO: 7)
5'-TCAGGAAAAAATGCGGATGGCCTGAGTGAC-3'

Mouse GAPDH primer Forward:
                                        (SEQ ID NO: 8)
5'-AGAGACAGCCGCATCTTCTT-3'

Mouse GAPDH primer Reverse:
                                        (SEQ ID NO: 9)
5'-GACAAGCTTCCCATTCTCGG-3'
```

As a result of the above quantitative RT-PCR, the effect of inhibiting mRNA expression of the MEX3B gene by the gapmer type nucleic acid of Comparative Example, which is complementary to a sequence included in CDS of the MEX3B gene, was found to be approximately 50%. However, as shown in FIG. 1(b), as the cytotoxicity was strong and many cells were peeled and detached from the bottom of the culture dish, it was observed that many cells have perished.

On the other hand, with the gapmer type nucleic acid of Example, the effect of inhibiting mRNA expression equivalent to the gapmer type nucleic acid of Comparative Example was obtained, and also a side effect such as cytotoxicity was not exhibited.

Example 2

<Preparation of Gapmer Type Nucleic Acid>

A gapmer type nucleic acid hmrGD-176 (SEQ ID NO: 11), hmrGD-178 (SEQ ID NO: 12), hmrGD-179 (SEQ ID NO: 13), hmrGD-180 (SEQ ID NO: 14), hmrGD-182 (SEQ ID NO: 15), hmrGD-199 (SEQ ID NO: 16), hmrGD-201 (SEQ ID NO: 17), hmrGD-202 (SEQ ID NO: 18), hmrGD-203 (SEQ ID NO: 19), or hmrGD-205 (SEQ ID NO: 20), which are an antisense oligonucleotide complementary to each target sequence shown of 3'UTR in Table 1, a gapmer type nucleic acid (SEQ ID NO: 21) as a negative control, and a gapmer type nucleic acid hmrGD-68 (SEQ ID NO: 22), which is an antisense oligonucleotide complementary to the target sequence shown in Table 1 of CDS region as a positive control, were prepared.

Furthermore, at both ends of each gapmer type nucleic acid, 2 bases of LNA (2',4'-BNA) were added and common DNA was employed as bases filling other gaps while the phosphodiester bond connecting each nucleotide was phosphorothioated. Total length of the gapmer type nucleic acid as a negative control was set at 15 bases and total length of the gapmer type nucleic acid other than that was set at 16 bases.

TABLE 1

| Gapmer type nucleic acid | SEQ ID NO | Gapmer sequence | Oligo length | Target sequence | Target area (Human pre-mRNA) | Target area |
|---|---|---|---|---|---|---|
| hmrGD-176 | 11 | GTACATTTAAGCTCAA | 16 | TTGAGCTTAAATGTAC | 4119-4134 | 3'UTR |
| hmrGD-178 | 12 | GCTCAGTAAAGTACAT | 16 | ATGTACTTTACTGAGC | 4129-4144 | 3'UTR |
| hmrGD-179 | 13 | ACTTTGCTCAGTAAAG | 16 | CTTTACTGAGCAAAGT | 4134-4149 | 3'UTR |
| hmrGD-180 | 14 | TTTAAACTTTGCTCAG | 16 | CTGAGCAAAGTTTAAA | 4139-4154 | 3'UTR |
| hmrGD-182 | 15 | CATAAAATAAAATATA | 16 | TATATTTTATTTTATG | 4163-4178 | 3'UTR |
| hmrGD-199 | 16 | AAAAATAAAACTCTTG | 16 | CAAGAGTTTTATTTTT | 4248-4263 | 3'UTR |
| hmrGD-201 | 17 | TAAATGTCAGAAAAAT | 16 | ATTTTTCTGACATTTA | 4258-4273 | 3'UTR |
| hmrGD-202 | 18 | AACTTTAAATGTCAGA | 16 | TCTGACATTTAAAGTT | 4263-4278 | 3'UTR |
| hmrGD-203 | 19 | TGTAGAACTTTAAATG | 16 | CATTTAAAGTTCTACA | 4268-4283 | 3'UTR |
| hmrGD-205 | 20 | ACCTTTATTATGTAGA | 16 | TCTACATAATAAAGGT | 4278-4293 | 3'UTR |
| Negative control | 21 | AACACGTCTATACGC | 15 | — | — | — |
| hmrGD-68 | 22 | GCGGGCAGCTGGTGCC | 16 | GGCACCAGCTGCCCGC | 2575-2590 | CDS |

<Transfection of Gapmer Type Nucleic Acid>

Transfection was carried out in the same manner as Example 1 except that each gapmer type nucleic acid which has been prepared above is used.

<Quantitative RT-PCR Test>

Quantitative RT-PCR test was carried out in the same manner as Example 1 except that the following primers are used as a PCR primer.

```
Human MEX3B primer Forward:
                            (SEQ ID NO: 23)
5'-ACCCAGTTCTGAGCATGTCG-3'

Human MEX3B primer Reverse:
                            (SEQ ID NO: 24)
5'-CGAACTGGGGTCTTGATGTAA-3'

Human GAPDH primer Forward:
                            (SEQ ID NO: 25)
5'-GCACCGTCAAGGCTGAGAAC-3'

Human GAPDH primer Reverse:
                            (SEQ ID NO: 26)
5'-TGGTGAAGACGCCAGTGGA-3'
```

Figure 2:
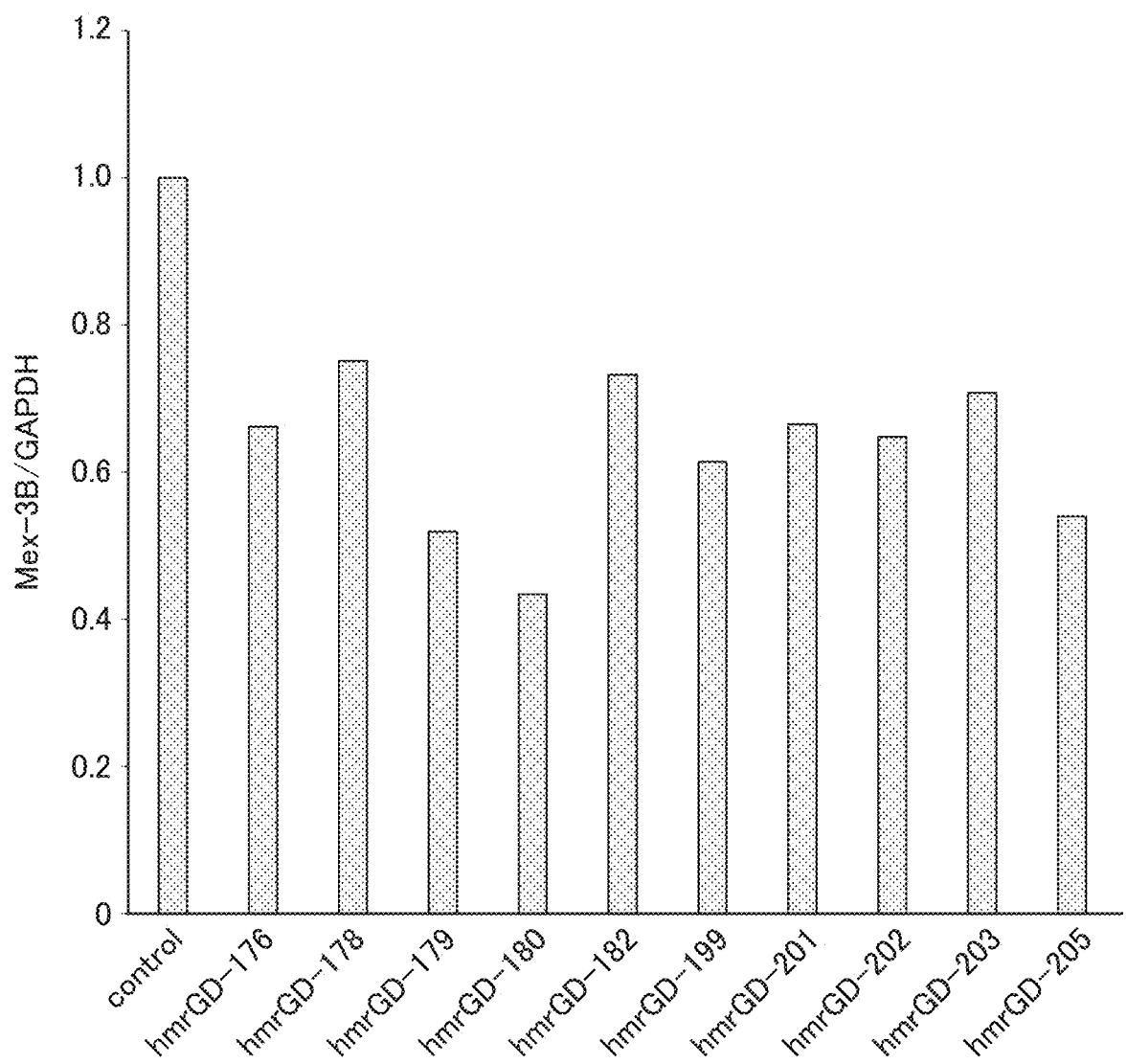
FIG. 2 is a view showing inhibition of the expression level of MEX3B mRNA caused by transfection with each gapmer type nucleic acid.

As it is evident from the result of the quantitative RT-PCR shown in FIG. 2, compared to the cells transfected with the gapmer type nucleic acid as a control, the effect of inhibiting mRNA expression of the human MEX3B was detected from the cells undergone with transfection by using each gapmer type nucleic acid hmrGD-176, hmrGD-178, hmrGD-179, hmrGD-180, hmrGD-182, hmrGD-199, hmrGD-201, hmrGD-202, hmrGD-203 or hmrGD-205, which have 3'UTR as a target area.

The effect of inhibiting mRNA expression of the human MEX3B was particularly strongly detected from the gapmer type nucleic acid hmrGD-179 which has a sequence complementary to an oligonucleotide of 4134 to 4149 positions, gapmer type nucleic acid hmrGD-180 which has a sequence complementary to an oligonucleotide of 4139 to 4154 positions, and gapmer type nucleic acid hmrGD-205 which has a sequence complementary to an oligonucleotide of 4278 to 4293 positions in SEQ ID NO: 10, which represents a pre-mRNA of the human MEX3B.

Figure 3:
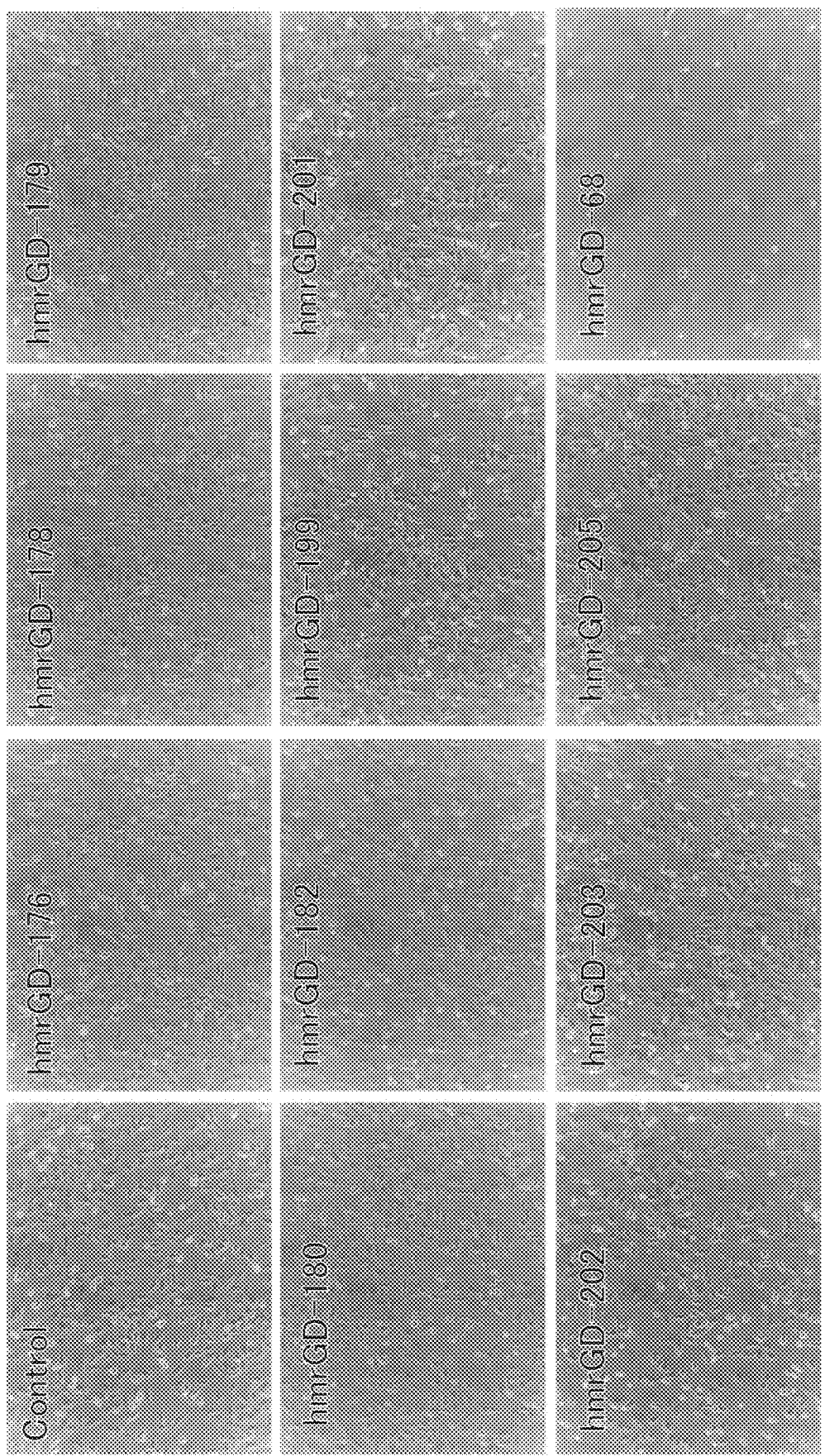
FIG. 3 is a view showing a microscopic image of cells having cytotoxicity caused by a gapmer type nucleic acid targeting CDS, and a microscopic image of cells having no cytotoxicity caused by a gapmer type nucleic acid targeting UTR.

As it is shown in FIG. 3, in the cells in which the transfection has been carried out by using the gapmer type nucleic acid hmrGD-68 which is complementary to the sequence of CDS region, the cytotoxicity was significantly high and many cells were peeled and detached in round form from the bottom of the culture dish, and thus it was confirmed that many cells have perished.

On the other hand, as it is shown in FIG. 3, from the cells in which the transfection has been carried out by using the gapmer type nucleic acid hmrGD-176, hmrGD-178, hmrGD-179, hmrGD-180, hmrGD-182, hmrGD-199, hmrGD-201, hmrGD-202, hmrGD-203, or hmrGD-205 which are complementary to the sequence of UTR region, a side effect such as cytotoxicity was not exhibited, similar to the negative control.

Sequence Listing

The invention claimed is:

1. A method for inhibiting expression of MEX3B gene comprising administering a nucleic acid to a subject, wherein the nucleic acid is a nucleic acid inhibiting expression of MEX3B gene which is an antisense oligonucleotide having a sequence complementary to an oligonucleotide that comprises 12 to 20 contiguous nucleotides in an untranslated region in an exon of the MEX3B gene.

* * * * *